US009308227B2

(12) United States Patent
Lang et al.

(10) Patent No.: US 9,308,227 B2
(45) Date of Patent: Apr. 12, 2016

(54) LACTIC ACID BACTERIA AND COMPOSITIONS CONTAINING THEM AGAINST BACTERIAL COLDS

(75) Inventors: Christine Lang, Berlin (DE); Andreas Raab, Berlin (DE); Natalia Bolotina, Berlin (DE)

(73) Assignee: ORGANOBALANCE MEDICAL AG, Berlin (DE)

( * ) Notice: Subject to any disclaimer, the term of this patent is extended or adjusted under 35 U.S.C. 154(b) by 196 days.

(21) Appl. No.: 14/118,091

(22) PCT Filed: May 16, 2012

(86) PCT No.: PCT/EP2012/059213
§ 371 (c)(1),
(2), (4) Date: Nov. 15, 2013

(87) PCT Pub. No.: WO2012/156491
PCT Pub. Date: Nov. 22, 2012

(65) Prior Publication Data
US 2014/0065218 A1 Mar. 6, 2014

(30) Foreign Application Priority Data
May 16, 2011 (EP) .................................... 11166203

(51) Int. Cl.
| A61K 35/744 | (2015.01) |
| C12Q 1/04 | (2006.01) |
| C12R 1/225 | (2006.01) |
| A61K 35/74 | (2015.01) |
| A23L 1/30 | (2006.01) |
| C12N 1/20 | (2006.01) |
| A23K 1/00 | (2006.01) |
| A61K 35/747 | (2015.01) |
| A61K 45/06 | (2006.01) |

(52) U.S. Cl.
CPC ................. *A61K 35/74* (2013.01); *A23K 1/008* (2013.01); *A23K 1/009* (2013.01); *A23L 1/3014* (2013.01); *A61K 35/744* (2013.01); *A61K 35/747* (2013.01); *A61K 45/06* (2013.01); *C12N 1/20* (2013.01); *C12Q 1/04* (2013.01); *C12R 1/225* (2013.01); *A23V 2002/00* (2013.01)

(58) Field of Classification Search
None
See application file for complete search history.

(56) References Cited

U.S. PATENT DOCUMENTS

| 7,846,711 B2 | 12/2010 | Boettner et al. | |
| 2002/0009436 A1* | 1/2002 | Doyle et al. | ................. 424/94.6 |

FOREIGN PATENT DOCUMENTS

WO 2007073709 A1 5/2007

OTHER PUBLICATIONS

Keller Mette Kirstine et al: "Co-aggregation and growth inhibition of probiotic lactobacilli and clinical isolates of mutans streptococci: An in vitro study", in: Acta Odontologica Scandinavica, Oslo, No, vol. 69, No. 5, Feb. 9, 2011, pp. 263-268.
Twetman Lisa et al: "Coaggregation between probiotic bacteria and caries-associated strains: An in vitro study", in: Acta Odontologica Scandinavica, Oslo, No, vol. 67, No. 5, Sep. 1, 2009, pp. 284-288.
Eva M Söderling et al: "Probiotic Lactobacilli Interfere with Biofilm Formation In Vitro", in: Current Microbiology, Springer-Verlag, NE, vol. 62, No. 2, Sep. 11, 2010, pp. 618-622.
Lang C et al: "Specific Lactobacillus/Mutans Streptococcus co-aggregation", in: Journal of Dental Research, International & American Association for Dental Research, vol. 89, No. 2, Feb. 1, 2010, pp. 175-179.
Guglielmetti Simone et al: "Oral Bacteria as Potential Probiotics for the Pharyngeal Mucosa", in: Applied and Environmental Microbiology, American Society for Microbiology, US, vol. 76, No. 12, Jun. 1, 2010, pp. 3948-3958.
Guglielmetti Simone et al: "A Dairy Bacterium Displays In Vitro Probiotic Properties for the Pharyngeal Mucosa by Antagonizing Group A Streptococci and Modulating the Immune Response", in: Infection and Immunity, American Society for Macrobiology, vol. 78, No. 11, Nov. 1, 2010, pp. 4734-4743.
L. Maudsdotter et al: "Lactobacilli Reduce Cell Cytotoxicity Caused by *Streptococcus pyogenes* by Producing Lactic Acid That Degrades the Toxic Component Lipoteichoic Acid", in: Antimicrobial Agents and Chemotherapy, vol. 55, No. 4, Apr. 1, 2011, pp. 1622-1628.
Rickard Alexander H et al: "Bacterial coaggregation: An integral process in the development of multi-species biofilms", in: Trends in Microbiology, Elsevier Science Ltd., Kidlington, GB, vol. 11, No. 2, Feb. 1, 2003, pp. 94-100.

* cited by examiner

*Primary Examiner* — Allison Fox
(74) *Attorney, Agent, or Firm* — Joyce von Natzmer; Agris & von Natzmer LLP

(57) ABSTRACT

The invention describes a microorganism of the order of lactic acid bacteria or an analog, fragment, derivative, mutant or combination thereof, wherein the microorganism, or analog, fragment, derivative, mutant or combination thereof can coaggregate with *Streptococcus pyogenes*.

28 Claims, 4 Drawing Sheets

LACTIC ACID BACTERIA AND COMPOSITIONS CONTAINING THEM AGAINST BACTERIAL COLDS

CROSS-REFERENCE TO RELATED APPLICATIONS

This is the U.S. national stage of International application PCT/EP2012/059213, filed May 16, 2012 designating the United States and claiming priority to European application EP 11166203.7, filed May 16, 2011.

The present invention relates to a microorganism of the order of lactic acid bacteria or an analog, fragment, derivative, mutant or combination thereof, wherein the microorganism or analog, fragment, derivative, mutant or combination thereof can coaggregate with *Streptococcus pyogenes*. In addition, the invention relates to compositions containing these microorganisms, in particular for use in personal hygiene and in treating diseases. In particular the present invention relates to the use of novel lactic acid bacteria and/or the compositions containing same for treatment and/or prevention of all diseases that can be caused by *Streptococcus pyogenes*.

In addition, the development described here is an innovative biological product in the form of GRAS microorganisms and/or lactic acid bacteria, which can be used an antimicrobial additive with a specific action for prevention and local treatment of inflammations in the area of the mouth and throat, i.e., the oropharyngeal space, and for infections of the upper respiratory tract and of the skin.

Furthermore, the present invention relates to the use of the microorganism according to the invention, an analog or fragment thereof in compositions or pharmaceutical products or medical products (oral hygiene), for example, in the form of sprays, mouth washes or as throat lozenges or tablets, pastilles, coated pills, aerosols, toothpastes, juices, syrups or as an additive to foods and/or as food supplements.

BACKGROUND

Most people have already had a sore throat or tonsillitis (pharyngitis). These diseases may have both viral and bacterial causes. Approximately 20-30% of the cases of sore throat and tonsillitis are of bacterial origin. In any case, this involves an infection by *Streptococcus pyogenes*. *Streptococcus pyogenes* is one of the most common human pathogenic bacteria. Bacterial pharyngitis is spread by droplet infection. Children and teenagers between the ages of 5 and 15 are the group most commonly affected by this infection but the elderly are also at risk of infection in crowded human conditions (Bisno 1995). The number of *S. pyogenes* infections in the United States is estimated at 10 million per year (Kilian 2002). The associated costs are estimated at approx. 1 billion dollars annually in the Unites States (Reid et al. 2001). The number of acute streptococcal pharyngitis cases in Germany is estimated at 1 to 1.5 million per year. Only a portion of the infections have a clinically manifest course, i.e., the reservoir of transmitted pathogens is larger.

*Streptococcus pyogenes* (group A streptococci, also referred to as GAS) is a human pathogen belonging to the Gram-positive cocci that form long chains. Like many other pathogens, streptococci also have the ability to express multiple virulence factors. The first step in the course of pathogenesis of *Streptococcus pyogenes* is adhesion of the bacteria to the surface of the host cells. According to a widely accepted model, adhesion takes place in two stages: the first stage consists of a weak, relatively nonspecific interaction with the surface of human cells, which immediately results in a tissue-specific interaction with a high affinity (Hasty et al. 1992; Courtney et al. 1999; Cunningham 2000). As early as 1976, Beachey et al. were able to identify lipoteichoic acid (LTA) as a molecule that mediates the initial adhesion on a bacterial level. On the epithelial level, fibronectin has been identified as the receptor for LTA (Simpson and Beachey 1983). At least 11 other structures on the bacterial surface have been identified as imparting binding to the epithelial cells for the second stage of adhesion. The second step in pathogenesis due to *Streptococcus pyogenes* is the invasion of the bacteria into the epithelial host cells (LaPenta et al. 1994). LaPenta and colleagues have shown that GAS can infect human epithelial cells with frequencies that are sometimes higher than those of traditional intracellular human pathogens such as *Salmonella* or *Listeria*.

Pathogenic bacteria inside a host cell have a high potential for replication, which can result in an acute infection. Survival in a dormant state may lead to renewed occurrence of bacterial infections of the mucous membranes and the epithelium, which can explain recurring infections of the oropharyngeal mucosa. Angina in particular is a recurring infection that is very often caused by GAS in children.

*Streptococcus pyogenes* is the etiologic agent of many acute diseases such as pharyngitis, scarlet fever, impetigo, cellulitis. Invasive toxigenic infections, such as necrotizing fasciitis, myositis and *Streptococcus*-induced toxic shock syndrome as well as the development of immunomediated sequelae such as rheumatic fever and glomerulonephritis, are all caused by *Streptococcus pyogenes*.

It is estimated that between 5% and 15% of the population in general are carriers of this bacterium (usually in their throats) without any signs of disease. As a component of the normal flora, *Streptococcus pyogenes* can cause an infection when the immune system is weakened. Colonization of tissue (e.g., the respiratory tract or skin) with *Streptococcus pyogenes* follows the outbreak of the disease, associated with the relevant symptoms such as a scratchy throat, a sore throat and difficulty in swallowing.

Furthermore, infections with *Streptococcus pyogenes* can lead to complications due to spreading of the infection to the lower respiratory tract (otitis media, sinusitis, pneumonia) or into the blood stream and to meningitis as well as infections of the bones (osteomyelitis) and the joints (arthritis).

One element in colonization is bacterial adhesion to a cell surface and/or to the mucosal surface. The bacterium has a large repertoire of adhesions which mediate the binding to cell surfaces (e.g., M protein, fibronectin-binding protein, LTA, collagen-binding protein). The interaction, i.e., binding to cell surfaces, plays an initial role in the colonization of host cells as well as in the pathogenesis of *Streptococcus pyogenes*.

Accordingly, the early use of therapeutic agents for prevention and treatment are of crucial importance to reduce the total GAS microbe count and to efficiently prevent the binding, i.e., invasion of *Streptococcus pyogenes*.

Therapeutic agents capable of relieving the symptoms caused by *Streptococcus pyogenes* in the throat area have been described in the prior art.

PRIOR ART

The standard treatment of an acute disease is to administer antibiotics. Because of the increased incidence of penicillin resistance since the middle of the 1980s, among other reasons, this disease has again been on the advance in industrial countries in recent decades (Kaplan 1991; Musser and Krause 1998). There is no prevention because so far no functioning vaccine has been developed. This is due to the diversity of the main antigen used, the M protein from the bacterial cell wall and the immunological cross-reactivity of the other antigen candidates with human proteins.

It has been shown in general that the infection subsides in most patients anyway despite treatment with antibiotics (usually penicillin or erythromycin), which can have massive side effects.

The preparations currently available on the market essentially include lozenges, tablets, throat washes and throat sprays, in some cases mixed with local anesthetics (lidocaine, benzocaine), which bring brief relief from symptoms in the throat area, but these preparations do not kill *Streptococcus pyogenes*.

Lactic acid bacteria are generally used as probiotic bacteria for protection against gastrointestinal diseases caused by pathogens because they frequently also produce antibacterial substances in addition to lactic acid. *Lactobacilli* (lactic acid bacteria) are Gram-positive anaerobic to aerotolerant bacteria that are capable of metabolizing sugar to lactic acid (lactic acid fermentation). These include the families Lactobacillaceae, Aerococcaceae, Carnobacteriaceae, Enterococcaceae, Leuconostocaceae and Streptococcaceae. These are considered to be apathogenic and are used as probiotic bacteria in general to improve gastrointestinal flora and in the treatment of gastrointestinal symptoms. *Lactobacilli* are important in particular for the food industry, where they play an important role in the area of "functional food." In the past, the *Bifidobacterium bifidum* species was classified with the lactobacilli (*Lactobacillus bifidum*), but according to today's understanding, this species is not closely related phylogenetically to that order. However, it is still considered to be a lactic acid bacterium with regard to the metabolism. Lactic acid bacteria are also extremely important in the food industry because they are used to produce milk products, but they may also occur as pests (e.g., in a beer brewery). Lactic acid bacteria are classified as apathogenic.

The use of probiotic bacteria for a variety of applications has been described in the prior art. For example, WO 2010/130563 discloses the use of probiotic bacteria for dishwashing agents, thereby reducing the negative consequences of hand dishwashing for the skin. Furthermore, these bacteria have a protective effect on skin.

Use of such microorganisms in cosmetic skin treatment agents is already known. For example, U.S. Pat. No. 6,790,434 describes the use of such microorganisms in cosmetic skin treatment agents in combination with an extract of plant extracellular matrix to counteract the skin damage caused by UV radiation. However, the use of these microorganisms in detergents and cleaning agents is not disclosed there.

In addition, the use of certain *Bacillus* species in sanitary cleaning agents is also known. Thus WO 97/25865 describes the use of *Bacillus* species in cleaning agents for sanitary purposes, where they are supposed to prevent the reproduction of pathogens and to degrade organic soiling. The disclosed uses often involve inactivated bacteria in the form of spores. The spores are reactivated by substrates and should not reproduce due to genetic defects. However, the disadvantage here is that the reproduction and/or mutation of bacteria cannot be completely ruled out, so there remains a residual risk that the bacteria might also reproduce in an uncontrolled manner.

Meanwhile, an oral dosage form of probiotic bacteria has been disclosed in WO 2005/117921, where the dosage form contains at least one genus of probiotic microorganisms, where the dosage form and/or the bacteria is/are provided with a coating that contains cellulose ether.

In vitro experiments have shown that a few strains of *Lactobacillus* are capable of preventing the binding of GAS to human cell lines. The *Lactobacillus* strains compete with GAS for surface structures on the cells and thus prevent GAS from invading the host cells. Adhesion of *Streptococcus pyogenes* to the host cell is the first step in pathogenesis, and the invasion process into the host cells takes place in very short order, so this method is considered a disadvantage in the treatment of GAS infections. Coaggregation of planktonic *Streptococcus pyogenes* cells would be desirable here before binding to the cell surface takes place and an immune response can be induced.

The object of the present invention is to provide an agent or composition for treatment and prevention of infections by *Streptococcus pyogenes* that does not have the shortcomings or disadvantages of the prior art.

SUMMARY OF THE INVENTION

This object is achieved by the independent claims. Advantageous embodiments are derived from the dependent claims.

In a first aspect, the invention relates to a microorganism of the order of lactic acid bacteria or an analog, fragment, derivative, mutant or combination thereof, where the microorganism or analog, fragment, derivative, mutant or combination thereof can coaggregate with at least one pathogenic microorganism, such that the pathogenic microorganism is *Streptococcus pyogenes*. It was completely surprising that a microorganism that binds to *Streptococcus pyogenes* could be made available, this microorganism being a lactic acid bacterium. In an especially preferred embodiment, the microorganism or the analog, fragment, derivative, mutant or combination thereof belongs to the *Lactobacillus* genus.

It was also completely surprising that in a preferred embodiment with the microorganism or analog, fragment, derivative, mutant or combination thereof, the coaggregation ability of the pathogenic microorganism exists even after a biological, chemical or physical treatment. The coaggregation ability of the pathogenic microorganism exists even at a pH between approx. 3 and approx. 8. It is preferable for the microorganism or analog, fragment, derivative, mutant or combination thereof to have the ability to inhibit the formation of a biofilm of the pathogenic microorganism. It is also preferable that for microorganism or analog, fragment, derivative, mutant or combination thereof to have the ability to prevent //the binding of *Streptococcus pyogenes* //from binding// to fibronectin. In a preferred embodiment, the microorganism or analog, fragment, derivative, mutant or combination thereof does not have the ability to coaggregate with commensal microorganisms of the skin or mucous membranes.

This microorganism is preferably selected from the group comprising *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentosus, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus fermentum, Lactobacillus reuteri, Lactobacillus viridescens, Bifidobacterium bifidum, Lactobacillus ingluviei* or analogs, derivatives, fragments or mutants thereof.

The microorganism is advantageously selected from the group consisting of the following microorganisms that have been deposited in accordance with the Budapest Treaty with the German Collection for Microorganisms and Cell Cultures ("DSM" located Inhoffstrasse 7B, 38124 Braunschweig, Germany), an international deposit authority under the Budapest Treaty having been assigned deposit numbers DSM 25972, DSM 25987, DSM 25988, DSM 25989, and DSM 25973.

In another aspect, the invention relates to a composition comprising at least one microorganism or analog, fragment, derivative, mutant or combination thereof. The composition may preferably comprise a pharmaceutically or cosmetically acceptable vehicle or excipient. It is preferable for the composition to be present in solid, liquid, viscous form or as an aerosol. The composition is preferably in the form of pastes, soft gelatin capsules, hard gelatin capsules, powders, granules, beads, pastilles, effervescent tablets, lozenges, buccal tablets, chewable tablets, sublingual tablets, solutions, tinctures, emulsions, juices, concentrates, syrups, sprays, drinking ampoules, gels, mouth washes, toothpowders, chewing gum, tablets, coated pills or bonbons.

The composition may advantageously comprise probiotics, antiseptics or other active antibacterial substances and/or may preferably also contain one or more of the following substances selected from antioxidants, vitamins, coenzymes, fatty acids, amino acids and cofactors.

In a preferred embodiment of the invention, the composition is a pharmaceutical, veterinary or cosmetic composition or a food supplement or a food supplement composition. The composition preferably contains one or more thickeners, one or more sweeteners and/or one or more artificial sweeteners, wherein the thickener is preferably selected from cellulose ether, polysaccharides, selected from the group comprising xanthan gum, gelatin, highly dispersed silicon dioxide, starch, alginates, tragacanth, agar, gum arabic, pectin and polyvinyl esters, and the sweetener is selected from the group comprising glucose, fructose, sucrose and glucose syrup, sorbitol, mannitol, xylitol and maltitol, saccharine, sodium cyclamate, acesulfame K and/or aspartame.

Preferred pharmaceutical products in the sense of the invention include nasal rinses, mouth washes and dental rinses; gargle solutions, nose sprays, mouth sprays, throat sprays, nose drops, drops, tinctures, juice or syrup for coughs, sore throats, colds or infections in the mouth, throat or neck area, throat tablets, bonbons, chewable bonbons, coated pills and pastilles for throat symptoms or sore throats as well as aerosols.

Preferred medical products in the sense of the invention comprise nasal rinses, mouth washes and dental rinses; gargle solutions, nose sprays, mouth sprays, throat sprays, nose drops, drops, tinctures, juice or syrup for coughs, sore throats, colds or infections in the mouth, neck or throat area, throat tablets, bonbons, chewable bonbons, coated pills and pastilles for throat symptoms or sore throats as well as aerosols.

Preferred cosmetic products in the sense of the invention comprise toothpaste, lotion, shake mixes, powders, nose washes, mouth washes and dental washes, gargle solutions, nose sprays, mouth sprays, throat sprays, chewing gum, hydrogel, creams, cresa, ointment, fat-based ointment or paste for application to a skin surface.

Preferred foods and nutritional supplements in the sense of the invention comprise effervescent tablets, vitamin tablets, mineral tablets, trace element tablets, beverage powders, beverages, juices, milk beverages, yogurts, mineral water, uncarbonated water, bonbons, chewable bonbons, chewing gum, juice or syrup, throat tablets, coated pills and pastilles as well as aerosols. Furthermore, the composition may also contain builders, enzymes, electrolytes, pH regulators, thickeners, soil release agents, optical brighteners, graying inhibits, dye transfer inhibitors, foam regulators and/or coloring agents.

The microorganisms may advantageously be present in viable or killed form in the composition. In addition, it may be preferable for the microorganism to be present in an encapsulated, spray-dried and/or lyophilized form, and it may also be preferable for the microorganism to be present in the form of a cell lysate. In addition, it is preferable for the microorganism to be present in the composition in an amount with an amount by weight of 0.001 wt % to 20 wt %, preferably 0.005 wt % to 10 wt %, especially preferably 0.01 wt % to 5 wt %.

In another aspect, the present invention relates to a method for identifying and/or selecting a lactic acid bacterium having the property of coaggregating *Streptococcus pyogenes*, where the method comprises at least the following steps:
  a. Incubating the pathogenic microorganism to form a biofilm,
  b. Adding a lactic acid bacterium to be tested and incubating it to form a mixture for developing the coaggregation between the pathogenic microorganism and the lactic acid bacterium to be tested,
  c. Separating the unbound lactic acid bacteria by removing the supernatant, and
  d. Determining the biofilm with regard to coaggregated lactic acid bacteria.

Furthermore, the method may additionally comprise the following process step:
  Investigating biofilm inhibition due to the pathogenic microorganisms, where the lactic acid bacteria to be investigated are added during incubation of the pathogenic microorganisms that form the biofilm, and/or preferably
  Quantification of biofilm formation after removal of the unbound cells by measuring the optical density in comparison with a control without addition of the lactic acid bacteria to be tested.

In addition, the invention relates to the use of the composition to produce a pharmaceutical drug, a medical product or a cosmetic for treatment, prevention and/or therapy for microbial disease of the skin, the mucous membranes and the oral cavity.

The preferred composition may also be used for topical prophylaxis and/or treatment of microbial diseases of inflammatory diseases of the skin, the mucous membranes and the oral cavity. It is preferable that the composition is used for prevention and/or treatment of microbial diseases of the oral cavity and also comprises one or more flavoring substances. In addition, it is preferable for the composition to be used for topical prevention and/or treatment of microbial diseases or inflammatory diseases, preferably microbial diseases or inflammatory diseases of the oral cavity, wherein the composition is used in the form of a chewable mass, a chewing gum, a bonbon, a pastille, toothpaste or a mouth wash.

It may be advantageous that one or more anti-inflammatory or antimicrobial substances are used in the composition. In addition, it may be preferable for the composition to be used in combination with solvents, vehicles, excipients, fillers, flavoring substances, aroma substances and/or additional ingredients. In a preferred embodiment, the composition may be used to prepare a cleaning agent or a disinfectant for the treatment of surfaces. It is also preferable for the composition to be used for producing a product which is used in the field of medical products and/or prevention. It is preferable if the composition is used to prepare and agent for oral, sublingual, buccal ingestion.

In a preferred embodiment, the composition may be used to produce an antimicrobial additive for topical treatment of inflammations in the oropharyngeal space and for infections of the upper respiratory tract and of the skin. A preferred composition is used prophylactically or curatively in particular. It may be preferable if the composition is applied orally, sublingually or buccally.

Furthermore, the invention relates to a kit for a hygiene treatment comprising preferred microorganisms or a preferred composition for physical hygiene devices or appliances, rinses and/or pastes. The kit may be used for treatment of bacterial infections in the mouth or throat area, where the infections are caused by *Streptococcus pyogenes* in particular or this species is at least involved in the infection.

The present invention preferably relates to novel lactic acid bacteria, analogs, mutants, derivatives or fragments thereof as well as compositions containing them in particular for use for treatment or prevention in infants, toddlers, children, healthy persons, the elderly, immunosuppressed people, people with single-occurrence or recurring *Streptococcus pyogenes* infections and/or people with bacterial infections of the throat and tonsils (pharyngitis). The invention may surprisingly also be used for animals.

Accordingly, it is preferable to use the composition to prepare a pharmaceutical drug that is beneficial for the treatment or prevention of throat symptoms, sore throat, redness of the throat as well as purulent and nonpurulent inflammations of the throat and tonsils, in which the administration of lactic acid bacteria is desirable. The preferred composition may be used curatively or prophylactically, for example, as a probiotic.

The preferred microorganisms, namely the microorganisms belonging to the genus of lactic acid bacteria or analogs, derivatives, mutants or fragments thereof in particular have the capacity for coaggregation, with specific binding to *Streptococcus pyogenes*. It was completely surprising that the preferred lactic acid bacteria do not cause any coaggregation or binding of commensal microorganisms such as *Streptococcus salivarius*. *Streptococcus salivarius* is found on the mucous membranes in the throat area of healthy humans and contributes toward a healthy microbial equilibrium, so its aggregation is not preferred within the context of the present invention.

In other words, the preferred lactic acid bacteria coaggregate specifically with the pathogenic bacteria *Streptococcus pyogenes*. Nothing of this type can be derived from the prior art. The prior art describes only lactic acid bacteria that prevent the invasion and replication of *Streptococcus pyogenes* in and/or on human cell lines. However, adhesion is the essential first step in bacterial pathogenesis, so that this approach could not be used without having side effects. In contrast with that, the preferred lactic acid bacteria have a specific coaggregation with planktonic *Streptococcus pyogenes* cells, represented as an example on strains having the DSM numbers ATCC 12344 and ATCC 19615 before they can bind to the host cells. The present invention may thus be regarded as a departure from the usual, because there is a trend in the prior art toward reducing the binding of *Streptococcus pyogenes* to the epithelial cells. However, it has not been reported that the pathogenic cells can be coaggregated in the oral cavity, so that binding to epithelial cells cannot take place from the beginning. This also has the important advantage that the cell aggregates are swallowed with saliva or by means of a mouth wash, and the *Streptococcus pyogenes* cells are killed during gastrointestinal passage. This is therefore also a user-friendly application because it is generally perceived as unpleasant and inconvenient to spit out mouth wash, for example. Nothing of this type is necessary for the preferred use.

Those skilled in the art know that healthy skin and/or mucous membranes is/are densely populated with microorganisms such as bacteria and fungi, which are referred to as commensal and/or mutual. These microorganisms constitute a natural component of the skin surface and are referred to collectively as skin flora in particular. The microorganisms to be subsumed under the heading of autochthonic flora are an important prerequisite for protecting the skin itself and the body as a whole from pathogenic microorganisms and are part of the microbiome. In this regard, it is especially advantageous that the preferred lactic acid bacteria do not create an imbalance in the skin flora but instead merely bind to and/or coaggregate with the pathogenic bacterium *Streptococcus pyogenes*.

Not least of all, the microorganisms according to the invention prevent binding to fibronectin and thus prevent invasion of the cells. Due to the fact that the preferred lactic acid bacteria coaggregate with *Streptococcus pyogenes* and/or have adhesive properties with respect to these bacteria, this results in masking in particular and thus concealment of pathogenicity factors, which then leads to a reduction in bacterial load and/or to inhibition of the binding to fibronectin and/or to cells in the throat area.

Although the present invention relates to a group of lactic acid bacteria in particular, there is consistency in the teaching according to the patent application. The claimed microorganisms have a common property or effect. The sum of the structural or functional commonalities leads to the functional relationship of coaggregation of *Streptococcus pyogenes*, the nonbinding of commensal microorganisms of the skin and/or mucosa and preventing the binding to fibronectin by *Streptococcus pyogenes*. The common features therefore do not represent an arbitrary sum of features but instead constitute the common fingerprint of the claimed microorganisms, so to speak, which advantageously permits and characterizes the suitability of these microorganisms for this purpose. Furthermore, it has surprisingly been found that the surprising property of the microorganisms according to the invention, namely the coaggregation of *Streptococcus pyogenes*, is not inhibited either in saliva or in the presence of sugars. This is advantageous in particular because the preferred site of use of the microorganisms and the composition is in the oral cavity, and it is known from the prior art that coaggregation processes are generally inhibited by high sugar concentrations. However, tests have shown that this is not the case for the microorganisms according to the invention, in particular lactic acid bacteria, because these will still coaggregate with *Streptococcus pyogenes*, even at high sugar concentrations (such as those occurring in saliva, for example, as well as in possible dosage forms such as effervescent tablets, vitamin tablets, mineral tablets, trace element tablets, beverage powders, beverages, juice, milk beverages, yogurts, bonbons, chewable bonbons, chewing gum, juice or syrup, throat tablets, coated pills and aerosols).

It was also surprising that the preferred microorganism can also be used on skin, where it will also coaggregate with *Streptococcus pyogenes*. Those skilled in the art are aware that *Streptococcus pyogenes* is also known as a pathogenic wound organism, so it is especially advantageous that the coaggregation capability of the preferred microorganisms is not limited to the oral cavity but instead can also be applied to areas of the skin.

The present invention thus also relates to microorganisms, in particular lactic acid bacteria, analogs, mutants, derivatives or fragments thereof as well as compositions containing these, in particular for use for treatment or prevention in infants, toddlers, children, healthy people, elderly, immunosuppressed people, people with pathological skin changes (in particular staphylococcal scalded skin syndrome, impetigo contagiosa, folliculitis superficialis, impetiginization, skin abscesses, furuncles (furunculosis), carbuncles (abscesses), phlegmons, dry skin, itchy skin, reddened skin, irritated skin, extremely oily skin, acne, diabetic foot, decubital ulcers, neurodermatitis, acute lymphadenitis, pilonidal cysts (including pilonidal fistulas, pilonidal sinus, coccygeal fistula, coccygeal cysts), other local infections of the skin and the subcutaneous tissue (e.g., pyoderma, purulent dermatitis, septic dermatitis, suppurative dermatitis); they can also be used for treating the various forms of dermatitis and eczema (e.g., atopic eczema, seborrheic eczema, diaper rash or dermatitis, allergic contact dermatitis, seborrheic dermatitis, exfoliative dermatitis, toxic contact dermatitis, chronic lichen simplex, prurigo, pruritus and other forms of dermatitis); also papulosquamous skin diseases (psoriasis, parapsoriasis), diseases of the integumentary appendages (e.g., alopecia with scarring including folliculitis decalvans), plus other diseases of the skin and subcutaneous tissue (e.g., crural ulcers), people with pre-existing skin damage (e.g., dry skin), skin injuries (e.g., scabs, wounds, including those after accidents or surgery) in humans or in commercial animals and household pets.

In the sense of the present invention, the skin in preferred embodiments is understood in particular to be the external organ of the human or animal body which serves to delineate the inside from the outside. In preferred embodiments, a skin area in the sense of the present invention includes components of the top layer of skin, the corium or true skin or the subcutaneous tissue. The top layer of skin (epidermis) also consists of the following layers according to the invention: the stratum corneum (horny layer), the stratum lucidum (clear layer), the stratum granulosum (granular layer), the stratum spinosum (spinous layer) and/or the stratum basale (basal layer). Each modification of cells in this area constitutes a cell modification in an area of skin in the sense of the present invention. According to the invention, the dermis or corium, which may also be a component of the area of skin, preferably consists of connective tissue fibers and serves to provide nourishment and anchoring for the epidermis. The capillarized blood vessel system in the borderline zone with the epidermis also belongs to a skin area in the sense of the invention, as do the sebaceous glands and sudoriporous glands or sweat glands. The dermis in the sense of the present invention may be subdivided into a stratum papillare and a stratum reticulare. In addition, an area of skin in the sense of the invention may be any area, i.e., any location in or on the subcutaneous tissue (subcutis) or tissue in the interior of the body or any organ or organ component. A tissue barrier delineating an organ from the surrounding structures may be a skin in the sense of the present invention. In addition, the inventive concept of an area of skin may also be understood to include integumentary appendages such as hair, sebaceous glands, arrectores pilorum muscles, nails, horns and sudoriporous glands, in particular the eccrine and apocrine sudoriporous glands but also the mammary glands. Any cell modification, in particular a cell growth that deviates from the normal, can be treated with the agents according to the invention, preferably without being limited to the external areas of skin. However, the areas of skin in the sense of the present invention may also include the corium, such as that on the fingers or the soles of the feet, and the meshed skin and the integumentary appendages associated therewith.

The preferred composition may be contained in a soap, a lotion, a powder, a synthetic detergent or syndet, a foam, a stick, an emulsion, a spray, a cream, a gel, a shampoo, a liquid soap or a deodorant in particular. It is also preferable for the composition to be used in particular as a probiotic which may be added as a detergent, rinse agent, cleaning agent or disinfectant (e.g., soaps, powders, pastes, solutions, emulsions, lotions), cleaning and/or disinfection cloths or towels, shampoos, rinses or applications for the skin, hair and/or scalp, creams, ointments, skin cleaning lotions and/or skin care lotions, solutions (e.g., as drops, sprays, rinse) for use in or on the eyes, ears, mouth, nose or throat and/or may be incorporated into bandages or wound dressings to suppress the formation of pathogenic microorganisms, to bind them, to remove them as an aggregate and/or to inhibit them or to kill them and thereby to reduce their numbers.

It was completely surprising that the advantages of the composition according to the invention could be improved yet again by incorporating it into the aforementioned pharmaceutical forms. Those skilled in the art are familiar with other formulation concepts for introducing the composition according to the invention into vehicle substances, for example, such as emulsions or other products for dermal application, e.g., liquid forms, which may preferably be hydrous or anhydrous, where the aqueous forms can be divided into single-phase systems and multiphase systems according to the invention. In addition, semisolid forms which are anhydrous or hydrous may be used, where again it is possible to divide them into single-phase systems and multiphase systems in which semisolid forms containing water are also possible. Solid forms which are lipophilic or hydrophilic may preferably also be used. Examples of such forms include, for example, fat-based ointments, foams, powders, sticks, gel creams, hydrodispersion gels, thin (nonviscous) emulsions, lotions, ointments, sprays and creams in addition to those forms already mentioned above. Those skilled in the art are aware here that such vehicle substances can be differentiated first into those that are rich/high quality and those that are fresh and light, based on the feeling on the skin, and second, with regard to the viscosity, those with a low viscosity and others with a high viscosity, whereas hydrogels or hydrocreams and/or O/W emulsions or W/O emulsions have a high viscosity. When liquid application forms are used, they can be subdivided—as explained above—into hydrous and anhydrous systems. Of the anhydrous systems, apolar systems, polar systems without emulsifiers and polar systems with emulsifiers are especially preferred. Of the hydrous systems, single-phase systems such as solutions and microemulsions are preferred; of the multiphase systems, multiple emulsions W/O emulsions or O/W emulsions are preferred. Of the solid/liquid systems, preferred forms include suspensions or liquid/solid/liquid systems such as suspension systems/emulsion systems. Those skilled in the art know about various possibilities for supplying such vehicles. With the O/W emulsions, preferred leading pharmaceutical substances include O/W emulsifiers, W/O emulsifiers, liquid hydrophilic ingredients and liquid lipophilic ingredients. With the W/O emulsions, preferred pharmaceutical leading substances include W/O emulsifiers, O/W emulsifiers, liquid and semisolid lipophilic ingredients, gel-forming agents, liquid hydrophilic ingredients and/or salts.

Of the preferred semisolid vehicle substances, both hydrous systems and anhydrous systems are preferred for various applications. Anhydrous systems may consist of polar system or apolar systems without emulsifiers such as lipogels, oleogels or polyethylene glycol gels and/or may consist of apolar systems with emulsifiers on O/W absorption bases or W/O absorption bases. The hydrous systems may preferably consist of single-phase systems such as hydrogels or microemulsion gels or multiphase systems such as O/W creams, W/O creams or amphiphilic systems. The preferred semisolid preparations are spreadable preparations for application to the skin in the temperature range between room temperature and skin temperature or for application to the mucous membranes, where they have a topical effect, where they transport the active ingredients or have a softening or protective effect on the skin. Preferred preparations include ointments in the narrower sense, creams, gels and/or pastes. In addition to the ointments, creams, gels and pastes, oleogels may also be used as semisolid transparent single-phase systems. Those skilled in the art know of various anhydrous compounds for formulating semisolid systems from U.S. Pat. No. 6,187,323 or Aiache et al. 2001, including, for example, the compound of an olegogel and a hydrogel, which may be referred to as a bi-gel according to the present invention. In addition, hydrodispersion gels or various lipids may be used to provide vehicle substances according to the invention. When using lipids, organosilicon compounds like the organocarbon compounds may be used to supply lipid phases in disperse systems, where organocarbon compounds may be supplied, for example, with the help of nonhydrolyzable lipids or hydrolyzable lipids (glycerols) or wax esters. The advantages of such systems include an improved suppleness of the skin and an increase in its elasticity as well as the ability to have the effect of increasing release of the substances and penetration thereof, depending on the lipid composition. Those skilled in the art are familiar with which lipids they must use to increase or decrease, for example, the penetration within a time parameter.

Additional preferred vehicle substances include, for example, hydrodispersion gels and/or microcapsules, microspherules or pellets (macro beads). The vehicles mentioned serve to increase stability and ensure a minimum application period on the skin. The preferred semisolid single-phase systems can be prepared with the help of the following pharmaceutical leading substances: liquid hydrophilic ingredients in particular water and (poly)alcohols, hydrophilic gel-forming substances, salt-forming substances and W/O emulsifiers, O/W emulsifiers, liquid, semisolid and solid lipophilic ingredients as well as lipophilic gel-forming substances and builders. Those skilled in the art will know how they must combine these substances to achieve a certain effect.

Those skilled in the art will also know of other pharmaceutical preparations for dermal products. According to the present patent application, for example, all the pharmaceutical compounds disclosed in the citation by Daniels and Knie in JDDG; 2007, 5:367-383. Those skilled in the art are aware that different pharmaceutical preparations have different effects on the skin and they will apply galenic composition to the skin in different amounts. The contents of JDDG; 2007, 5:367-383 are herewith incorporated into the disclosure content of the teaching according to the patent application. Preferred products according to the invention include, for example, lipophilic or hydrophilic solutions, lipophilic or hydrophilic emulsions, lipophilic or hydrophilic suspensions, special liquid preparations, hydrophobic or hydrophilic ointments, water-emulsifying ointments, lipophilic, hydrophilic or amphiphilic creams, hydrogels, hydrophobic or hydrophilic pastes and/or powders.

The preferred microorganisms in particular lactic acid bacteria are selected from the group comprising *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentosus, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus fermentum, Lactobacillus reuteri, Lactobacillus viridescens, Bifidobacterium bifidum, Lactobacillus ingluviei* or analogs, derivatives, fragments or mutants thereof; these microorganisms are associated through the functional relationship with one another to form a uniform idea according to the invention, such that they share the properties and/or effects, namely that they specifically coaggregate the pathogenic bacterium *Streptococcus pyogenes*, do not bind any commensal microorganisms of the skin and/or mucous membranes and also prevent binding to fibronectin by *Streptococcus pyogenes* and/or they destroy the *Streptococcus pyogenes* cells that are bound to fibronectin. These lactic acid bacteria include in particular microorganisms or analogs, fragments, derivatives, mutants or combinations thereof selected from the group comprising the following microorganisms deposited with the German Collection for Microorganisms and Cell Cultures under the code numbers DSM 25972, DSM 25987, DSM 25988, DSM 25989, DSM 25973. It was completely surprising that a group of lactic acid bacteria could be identified that had identical advantageous properties. No bacteria, in particular no lactic acid bacteria that combine all these properties while also being apathogenic and not causing any damage to or influence on the natural flora of the skin have been described. It has also been found that application of the preferred lactic acid bacteria, whether as a composition or otherwise, prevents the binding and invasion of host cells by *Streptococcus pyogenes*. The cause of this is so far unknown but should be identified by additional experiments.

Another surprising advantage of the preferred microorganisms, in particular lactic acid bacteria is that they can also be used prophylactically. This means that the lactic acid bacteria and/or a composition containing them can be applied prophylactically (preferably in the form of lozenges or bonbons) without thereby damaging the mucous membranes of the mouth and throat or the autochthonic flora.

In the sense of the present invention, the skin and/or mucous membranes are preferably understood in preferred embodiments to refer in particular to the external organ of the human or animal body which serves to delineate the inside from the outside. An area of skin in the sense of the present invention includes in preferred embodiments components of the mucous membranes.

Tolerability of the lactic acid bacteria on the skin and mucous membranes is one of the prerequisites for successful treatment of bacterial inflammations, infections, diseases or symptoms in the area of the throat involving microorganisms of the *Streptococcus* group. The preferred composition should be introduced in particular as a probiotic in the form of lozenges, bonbons or coated pills, juice or syrup, rinse, spray or aerosol to suppress the formation of the leading pathogenic microorganism and its binding to host cells, to bind these pathogens, to remove them as an aggregate and/or to inhibit and/or kill them and thereby reduce their numbers.

The composition according to the invention is preferably used as a bonbon, lozenge or coated pill. First, formulation as a bonbon, lozenge or coated pill permits a recipe that will have a pleasant taste in most cases (including the addition of sugars, sugar substitutes, flavorings) and which will gain great acceptance among patients and consumers. Second, the saliva which is also secreted when sucking on the lozenge moistens the mucous membranes, so that some release is experienced when there are symptoms of sore throat or tonsillitis. The composition according to the invention is released slowly over a prolonged period of time when sucking on bonbons, lozenges or coated pills, and this is advantageous for the aspect of application. Furthermore, it is technically very easy to implement the incorporation of the composition according to the invention into a composition for bonbons, lozenges or coated pills. In this respect it was completely surprising that it was possible to make available microorganisms that would have an activity and body temperature but could survive a heat treatment at 70° to 90° C. in such a way that they would still have the preferred abilities, in particular coaggregation of *Streptococcus pyogenes* even after the treatment. This is advantageous in particular because temperatures of 70° C. are frequently reached in the production of bonbons so that it is advantageous for the use of the microorganisms or the composition in the form of bonbons that the microorganisms still have the ability to coaggregate even after production of the bonbons. Nothing of this type is known from the prior art. The preferred microorganisms thus have capabilities which definitely differentiate them from the known microorganisms. In addition, it was surprising that the bonbons having the composition with the microorganisms would dissolve more slowly in the mouth and thus the bonbon would achieve a better and longer-lasting effect. This was completely surprising for the inventors. Furthermore, experiments have shown that in particular through the slow release of the microorganism, essentially all the *Streptococcus pyogenes* cells in the oral cavity can be coaggregated.

Those skilled in the art know what is to be subsumed under the term "body temperature" and how it can be determined. The body temperature here relates essentially to humans and animals. Those skilled in the art are also familiar with the term "bonbon" and also know in which standard literature to look for ingredients or the method for preparation of a bonbon. The present invention is not limited to simple bonbons but instead the invention may fundamentally be combined with all bonbons with which those skilled in the art are familiar. Bonbons and their production are disclosed to those skilled in the art in corresponding freely accessible technical literature, for example, in *Candy Ind.* 27, 161 (1996); H. Hoffmann, W. Mauch, W. Untze, *Sugar and Sugar Products*, $2^{nd}$ edition, Behr's: Hamburg (2002); R. Lees, B. Jackson, *Sugar Confectionery and Chocolate Manufacture*, Leonard Hill Books: Plymouth (1999); Federal Association of the German Confectionery Industry (BDSI), editors, *Confectioner's Handbook*, Molberg, Bonn (2001); *Handbook for the Food Chemist*, Food Leader, Thieme, Stuttgart (1995).

Bonbons may be preferred in a variety of shapes, taste directions, consistencies and colors. They are usually bite-sized pieces. Bonbons may be solid or filled, round, oval, cuboid or cube-shaped. Depending on the residual water content, they are hard (hard caramels) or soft and chewable (soft caramels). Depending on the additives a distinction is made in particular between throat bonbons and cough bonbons, fruit, caramel and refreshing bonbons. The effects and taste of the bonbons may be determined by using herbal extracts, essential oils (for example, eucalyptus) and active ingredients such as menthol. In the case of fruit bonbons, flavoring substances and acid components may produce an individual taste. Natural fruit and plant extracts or food dyes may also be added to impart color to the bonbons. Caramel bonbons are prepared in particular from milk products such as condensed milk, butter and cream. By flavoring and adding various additives, taste variants such as nuts, almond, honey, cocoa, coconut and the like are possible. Furthermore, chewable bonbons, cut, embossed, cast or laminated bonbons are preferred. Advantageous bonbons may be provided with a variety of ingredients, for example, vitamins, amino acid, oils, herbs, fats, various carbohydrates or sugar substitutes, taste enhancers and/or emulsifiers. Hard bonbons in particular contain sucrose and glucose which are preferably produced by using odor-imparting and taste-imparting, coloring substances and substance which influence the properties of the bonbons. Because of the low residual water content of 1-3%, hard caramels have a hard and often glossy consistency. Hard caramels may also be produced without sugar by using sweeteners and sugar substitutes.

Soft caramels denote in particular a group of confectionery products which have a chewable consistency, in contrast with hard caramels, and which are produced with a water content of 6-10% from the main ingredients being sucrose, other types of sugar, sweeteners and/or sugar alcohols as well as glucose syrup by batchwise or continuous cooking, preferably also containing fat, milk ingredients, thickeners, emulsifiers, flavor and taste-imparting substances as additives. They may also be produced in a wide variety of shapes and colors, with and without filling.

In addition, it has proven advantageous if the bonbons have a multichamber system, such that vitamins or other cofactors are present in one chamber and the preferred microorganisms or composition is/are present in one or more additional chambers. Through this chamber system it is possible to ensure that the microorganisms are released at an optimal point in time and optionally in different doses. The vitamins or other cofactors can also promote the activity of the microorganisms. For example, it has surprisingly been found that cranberries have the effect of preventing the development of a biofilm, so they are an optimal supplement to the preferred microorganisms. Tests have shown that coaggregation of *Streptococcus pyogenes* is 50% more efficient if ingredients or a solution of cranberries is/are also present.

Tests have shown that the preferred lactic acid bacteria, in particular *Lactobacillus* cells, form coaggregates on coming in contact with *Streptococcus pyogenes* cells. Through the formation of coaggregates, *Streptococcus pyogenes* is prevented from colonizing and invading cells of the throat area in particular. The *Streptococcus pyogenes* cells, in particular their cell surface, is/are masked by the lactic acid bacteria, in particular *lactobacillus* cells, so that the *Streptococcus pyogenes* cells are preferentially no longer able to bind to the epithelial cells of the skin and mucous membranes. Inflammation reactions are prevented by the hindered binding of *Streptococcus pyogenes* to the epithelial cells of the skin and mucous membranes. It was completely surprising that it would be possible to supply microorganisms that would coaggregate with *Streptococcus pyogenes* at a very early stage and would thus prevent binding of *Streptococcus pyogenes* to epithelial cells from the beginning. This was completely surprising and is not known in the prior art. The preferred microorganisms may thus already coaggregate with *Streptococcus pyogenes* in the oral cavity. Furthermore, it was completely surprising that the preferred microorganisms are not inhibited by the enzymes or other factors occurring in saliva, i.e., their *Streptococcus pyogenes* coaggregation capability is not inhibited.

Natural saliva contains, among other things, antimicrobial substances such as lysozyme, which serves as a defense against bacteria and can directly attack the cell wall of Gram-positive bacteria in particular. However, the preferred microorganisms are characterized in that despite the presence of natural saliva and despite the antimicrobial substances contained therein, they are still capable of specific coaggregation of *Streptococcus pyogenes*. This was completely surprising and is a considerable advantage over the prior art.

In the sense of the present invention, probiotic microorganisms comprise cells that have advantageous effects on the human and/or animal body. A preferred composition is used as a probiotic composition and contains lactic acid bacteria which have an advantageous effect on the human and/or animal body. Advantageous effects may consist in particular in the reduction of the microbial load of the neck and throat area by *Streptococcus pyogenes*. In particular unwanted microorganisms such as *Streptococcus pyogenes* in the autochthonic flora can be inhibited by indirect interactions with the probiotic microorganisms and the unwanted microorganisms and in particular by indirect interactions based on inhibition of the metabolism of the unwanted microorganisms by expression products of the probiotic microorganism. Tests have shown that the pathogenic *Streptococcus pyogenes* microorganism no longer exhibits any growth, i.e., there is no further reproduction of the cell mass after coaggregation with the preferred lactic acid bacteria but instead the cells are masked in particular and/or killed.

Another aspect of the present invention relates to analogs, mutants, derivatives or analogs or fragments of the lactic acid bacteria described here which are produced in particular by biological, chemical or physical treatment of the lactic acid bacteria and surprisingly exhibit the advantageous properties even after the treatment. The lactic bacteria are advantageously selected from the group comprising *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentosus, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus fermentum, Lactobacillus reuteri, Lactobacillus viridescens, Bifidobacterium bifidum, Lactobacillus ingluviei* and preferably selected from the group comprising the following microorganisms deposited with the German Collection for Microorganisms and Cell Cultures where they are numbered as DSM 25972, DSM 25987, DSM 25988, DSM 25989, DSM 25973.

Furthermore, it was surprising that the lactic acid bacteria, fragments, derivatives, mutants, analogs or combinations thereof would still have the advantageous properties even after physical, chemical and/or biological killing. For example, the preferred strains namely DSM 25972, DSM 25987, DSM 25988, DSM 25989 and DSM 25973 produce coaggregation of the pathogens, prevent binding to fibronectin and also do not exhibit any binding of commensal microorganisms even after a heat treatment at 70° C. for 20 minutes or a treatment with ultrasound. Thus the lactic acid bacteria, fragments, derivatives, mutants, analogs or combinations thereof may advantageously also be present in killed form in a preferred embodiment of the composition. In this way the stability and usability of the composition can be substantially prolonged. Furthermore, the composition is used in additional areas of application, which do not allow the use of viable microorganisms, are produced by thermal killing or lyophilization, in particular by biological, chemical or physical killing methods, whereby the analog or fragment still has the ability to specifically bind the pathogenic microorganisms even after killing or spray drying, said microorganism being selected from the group of *Streptococcus pyogenes*. It was completely surprising that the lactic acid bacteria are present in the composition in viable or nonliving (dead) form and nevertheless still specifically bind the pathogenic microorganism and/or coaggregate with it.

Furthermore, the present invention also relates to compositions containing the microorganism according to the invention or analogs or fragments or derivatives thereof which have the ability to specifically bind the pathogenic microorganism indicated above and which are used in particular as a food, food additive, animal feed or beverages. A preferred composition contains the lactic acid bacteria according to the invention or analogs, fragments, mutants or derivatives thereof which have the ability for specific binding and/or coaggregation of at least one pathogenic microorganism from the group of *Streptococcus pyogenes*, whereby the composition is used for the treatment of prevention of colds.

The preferred microorganisms according to the invention are representative of the genus of lactic acid bacteria, i.e., Gram-positive bacteria which produced lactic acid by fermentation of glucose. The microorganisms according to the invention are characterized in that on the one hand they have the ability to specifically bind, i.e., for coaggregation of at least one pathogenic microorganism selected from the group of *Streptococcus pyogenes*. This binding leads to the formation of aggregates of the microorganisms according to the invention and the specifically bound pathogenic microorganisms. Due to the formation of aggregates, the latter, i.e., the pathogenic microorganisms can be removed mechanically, for example, by rinsing them off in a targeted and easy procedure, which was impossible with the measures known in the past.

The term "specific binding" or "coaggregation" is understood in the sense of the invention as well as usually in the field of microbiology and hygiene, in particular human microbiology and physical hygiene and the mutual recognition and adhesion of cells belonging genetically to different types of cells. Coaggregation is understood in the sense of the invention in particular as adhesion, interaction, binding, specific binding, affinity or interaction and characterizes in particular the ability of the preferred microorganisms to form agglomerates with *Streptococcus pyogenes*. On their cell surface, the bacteria here express receptors and structures for adhesins to other cell types that are used for adhesion between the cells. This adhesion plays an excellent role in the colonization with pathogenic as well as with commensal microorganisms so that an intervention in the adherence could result in far-ranging consequences. Due to the fact that the microorganisms according to the invention have the capability for specific binding, in particular, coaggregation with at least one microorganism from the group of *Streptococcus pyogenes*, aggregates from the microorganisms according to the invention and the pathogenic microorganisms. The resulting coaggregates can be removed easily, for example, by rinsing surfaces, the skin, tissue and/or some other site or reservoir of colonization so that the number of pathogenic microorganisms is definitely reduced. In addition, an initial and/or renewed adhesion to surfaces, the skin, tissues and/or other sites or reservoirs of colonization are prevented and/or reduced by masking the surface structures of the pathogenic microorganisms. If cells bind to one another and form aggregates, this process is referred to as aggregation in particular. If only one cell species is involved in this formation of an aggregate, then that is referred to as autoaggregation or self-aggregation. If at least two different cell species are involved in formation of the aggregate, this process is known in particular as coaggregation.

In the sense of the present invention "specific binding of at least one pathogenic microorganism" is understood in particular to refer to the property of the microorganisms according to the invention to specifically bind at least one bacterium from the group of *Streptococcus pyogenes*.

According to a preferred embodiment of the microorganisms according to the invention, they are also characterized in that the ability for specific binding to at least one pathogenic microorganism exists even after a biological, chemical or physical treatment, for example, a heat treatment at a minimum of 70° C. In other words, the preferred lactic acid bacteria may preferably be present in killed form in a preferred composition because the ability for specific interaction or binding to pathogenic bacteria, in particular *Streptococcus pyogenes*, is not affected and thus a binding or interaction can be established.

The heat treatment mentioned above and/or "resistance to a heat treatment" or "thermal stability" is understood to refer to the property of a bacterium to still be capable of entering into a specific bond with at least one pathogenic microorganism selected from the group of *Streptococcus pyogenes* even after a certain length period of time of at least 30 minutes at an elevated temperature of 70° C. or more. Dead or killed lactic acid bacteria cells may be especially advantageous because the lactic acid bacteria cells cannot trigger any metabolic activity. "Dead or "killed" forms are characterized in particular in the sense of the invention in that these forms of the microorganisms according to the invention are no longer capable of division, for example, they cannot be stained with live living dyes, are not metabolically active and do not exhibit any DNA replication or protein biosynthesis or secretion, e.g., of metabolic products.

According to another preferred property of the lactic acid bacteria, the microorganisms according to the invention may also be characterized by a heat stability in addition to the property described above, namely the capability of specific binding of at least one pathogenic microorganism selected from the *Streptococcus pyogenes* group, and they can survive a treatment at high temperatures preferably at least approx. 60° C., more preferably at least 65° C. and even more preferably at least 70° C. for a period of at least 20 minutes, preferably 25 minutes and more preferably at least approx. 30 minutes and remain unchanged with respect to their capability for coaggregation of specific binding of the aforementioned pathogenic microorganisms.

In a preferred embodiment of the composition, lactic acid bacteria that are alive or killed or are parts and fragments, e.g., enzymatic or mechanical cleavage products (e.g., French press, etc.) or metabolic products of these bacteria are preferred, inasmuch as they still have the capability for coaggregation and/or for preventing the binding to fibronectin. It is also preferable for the lactic acid bacteria to be used in encapsulated, spray-dried and/or lyophilized form, i.e., to be present in encapsulated, spray-dried or lyophilized form in a preferred composition. Furthermore, it may be advantageous if the lactic acid bacteria are used in the form of digested cells.

Furthermore, it is preferable if the capability of the lactic acid bacteria according to the invention for specific binding of the pathogenic microorganisms also persists at a pH between approx. 3 and 8. This means that the lactic acid bacteria may be in a medium having a pH of 3 to 8 and still have their ability to bind *Streptococcus pyogenes*. The preferred lactic acid bacteria may advantageously be used in a wide pH range and/or they have the preferred properties in the preferred range. The preferred lactic acid bacteria may thus be used universally in different areas of the body. The lactic acid bacteria according to the invention have surprisingly exhibited coaggregation properties with *Streptococcus pyogenes* in particular in a broad temperature range of approx. 25° C.-42° C. It will thus be clear to those skilled in the art that here, as well as in all the statements of range given in the present invention, characterized by such terms as "about" or "approximately," that the precise numerical range need not be indicated with expressions such as "about" or "approx." or "approximately," but instead even minor deviations up or down with regard to the number indicated are still within the scope of the present invention. The binding of the lactic acid bacteria according to the invention to the pathogenic microorganisms listed preferably results in inhibition of the growth of the pathogenic microorganism.

It was surprising that by binding the pathogenic microorganism and the lactic acid bacteria according to the invention, an aggregate is formed, which can be centrifuged at a centrifugal force of preferably 300 g for 10 seconds in particular and then is present as a sediment, in particular after preferably 10 minutes of incubation at room temperature without agitation.

According to another preferred embodiment, the lactic acid bacteria according to the invention do not have the ability to bind to commensal oropharyngeal flora such as *Streptococcus salivarius*, where *Streptococcus salivarius* in particular is a largely unremarkable commensal of the flora of the skin. In the interaction of the various microorganisms present in or on the skin, this *Streptococcus pyogenes* species is present in the healthy skin flora of many mammals and is in a microbial equilibrium with them—at least on healthy skin. An influence on this bacterium due to aggregation, for example, and therefore an influence on other microorganisms that might be present in physical hygiene for a targeted purpose is not preferred within the scope of the present invention.

In a preferred embodiment, the present invention relates to lactic acid bacteria, analogs, fragments or derivatives thereof, whereby the lactic acid bacteria in a preferred embodiment comprise analogs, fragments, mutants, derivatives or combinations thereof, preferably having at least one of the following features: a) heat stability or stability after biological and/or chemical and/or physical treatment or b) ability to inhibit adhesion of host cells by *Streptococcus pyogenes*. It was completely surprising that the lactic acid bacteria according to the invention are still capable of binding *Streptococcus pyogenes* specifically even after biological and/or chemical and/or physical treatment.

Another property of the lactic acid bacteria according to the invention is the capability to inhibit binding to host cells by *Streptococcus pyogenes* in that these cells, which are already present in planktonic form, are specifically coaggregated and then washed away as aggregates. These pathogenic bacteria can no longer colonize and invade biological surfaces due to this coaggregation and therefore they also cannot cause any diseases.

Therefore in the sense of the present invention, the phrase "inhibiting the binding to host cells (oropharyngeal cells) by *Streptococcus pyogenes*" is to be understood to refer in particular to the property of the lactic acid bacteria according to the invention to interact with *Streptococcus pyogenes*, i.e., to bind to them or otherwise influence them in such a way that they can no longer bind to oropharyngeal cells.

According to a preferred embodiment, the microorganism according to the invention may therefore have at least one of the stated properties, i.e., resistance to biological, chemical and/or physical treatment, heat resistance, capability for specific binding, coaggregation to *Streptococcus pyogenes*. A preferred combination of properties would include, for example, two or three properties, i.e., for example, resistance to biological, chemical and/or physical treatment, heat resistance and capacity for binding to *Streptococcus pyogenes* or resistance to biological, chemical and/or physical treatment, heat resistance and inhibition of binding to oropharyngeal cells by *Streptococcus pyogenes*.

In the present case, as already stated, the expression "microorganism belonging to the genus of lactic acid bacteria" is also understood to include derivatives, mutants, analogs or fragments thereof which still have the characteristics and/or features or properties of the microorganisms according to the invention described here. The lactic acid bacteria according to the invention are preferably bacteria of the species *Lactobacillus paracasei* subspecies *paracasei*, *Lactobacillus plantarum*, *Lactobacillus crispatus* and *Lactobacillus ingluviei*.

Accordingly, "a mutant or a derivative" of the aforementioned microorganisms belonging to the genus of lactic acid bacteria, in particular a mutant or a derivative of the *Lactobacilli* sp. deposited with the DSMZ collection as part of the present patent application has the same characteristics as those claimed for the lactic acid bacteria according to the invention in the present case and in particular the same strains as those deposited with the DSMZ; this would refer at least to the capability for specific binding, coaggregation of at least one pathogenic microorganism selected from the group of *Streptococcus pyogenes*. In addition, it is preferable to have at least one of the following features: (i) resistance of the capability for specific binding to a biological, chemical and/or physical treatment, in particular a heat treatment at more than 70° C. for at least 30 minutes; (ii) no binding to *Streptococcus salivarius*; (iii) capability for specific binding to *Streptococcus pyogenes*; (iv) capability for inhibiting the binding to oropharyngeal cells by *Streptococcus pyogenes*; (v) existence of the specific binding at pH 3-8; (vi) capability for specific binding in natural saliva. Such preferred derivatives can be produced by genetic engineering, for example. The term "produced by genetic engineering" in the sense of the present invention includes in particular all methods with which those skilled in the art are familiar in the field of genetic engineering for modification of nucleic acids in vitro and in vivo, so that genetic modifications can be induced by recombinant DNA technologies and genes can be modified.

Accordingly, the present invention also includes in particular fragments of the lactic acid bacteria according to the invention, which still have the properties of the lactic acid bacteria according to the invention. A "fragment" in the sense of the present invention is in particular a cellular component of the microorganisms according to the invention and preferably a part of the cell membrane. Those skilled in the art will be adequately familiar with methods of obtaining cell membrane fractions from the prior art.

The microorganisms according to the invention are preferably in isolated or purified form, where the term "isolated" means in particular that the lactic acid bacteria are derived from their culture medium—including their natural medium, for example. The term "purified" is not restricted to absolute purity.

It is preferable that in addition to the microorganisms according to the invention in a viable form, killed forms of the microorganisms according to the invention are also included within the scope of the present invention. Suitable methods for killing (e.g., biological, chemical or physical killing methods) are sufficiently familiar to those skilled in the art. In the present case, however, the microorganisms may also be used in lyophilized form. Lyophilized cells can be made to grow again after suitable culturing in a liquid or solid medium. This was completely surprising and relates to a novel and inventive niche. The prior art includes, for example, solutions for cleaning surfaces that contain spores, where the bacteria are reactivated when the spores come in contact with corresponding substrates. Nothing of this type is necessary for the preferred microorganisms and the composition. The preferred microorganisms are also active, i.e., they coaggregate with *Streptococcus pyogenes* and also have other properties as described above, but they no longer have any metabolic activity and would be referred to by those skilled in the art in microbiology as being "dead." Thus the microorganisms are no longer capable of growing, dividing, replicating or secreting metabolic products, so their range of use is greatly enlarged.

The terms "killed" or "dead form" and "derivatives" or "analogs" or "mutants" also include in the present case lysates, fractions or extracts of the microorganisms according to the invention, where these lysates, fractions or extracts preferably have the properties of the lactic acid bacteria where "lysate"—as well as the term "extract"—refers in particular to a solution or suspension in an aqueous medium of the cells of the microorganism according to the invention and comprises, for example, macromolecules such as DNA, RNA, proteins, peptides, lipids, carbohydrates, etc. as well as cell detritus. The lysate preferably also includes the cell wall or cell wall constituents. Methods of producing lysates are sufficiently well known to those skilled in the art and includes, for example, the use of a "French press" or enzymatic lysis, a ball mill with glass beads or iron beads. Cells can be broken open by enzymatic, physical or chemical methods. Examples of enzymatic cell lysis may include individual enzymes as well as enzyme cocktails, for example, proteases, proteinase K, lipases, glycosidases; chemical lysis may be induced by ionophores, detergents such as SDS, acids or bases; physical methods may also be implemented by using high pressures such as the French press, osmolarities, temperatures or alternating between heat and cold. Furthermore chemical, physical and enzymatic methods may of course be combined. "Killed forms" or "dead forms" and "derivatives" or "analogs" or "mutants" of the microorganisms according to the invention preferably have the same properties as the aforementioned strains. The "killed form" or "dead form" and "derivative" or "analog" preferably no longer have any metabolic activity. Analogs of the microorganisms according to the invention are one form of the lysate or fragments. A fragment of the microorganisms according to the invention is a part of the cells, e.g., cell membrane, macromolecules such as DNA, RNA, proteins, peptides, lipids, carbohydrates, etc. as well as cell detritus. Mutants and/or genetically altered variants or derivatives are altered genetically, for example, by recombinant DNA technologies (cloning, sequencing, transformation of recombinant nucleic acids) as well as physical mutagenesis, for example, by ultraviolet radiation but also through chemical agents such as with ethyl methane sulfonate (EMS). Changes in the positive properties can be selected. Genetically altered mutants contain cells of the microorganisms according to the invention and retain recombinant nucleic acids in their bacterial chromosome and/or plasmids. Modifications through point mutations may also induce effects on the expression/transcription/translation as well as spontaneous mutations even without any direct genetic manipulation. Analogs or fragments may include thermally killed (dead) or lyophilized forms of the microorganisms according to the invention which retain their properties according to the invention or even improve them by enlarging the surface area, for example. Cells after lyophilization (freeze drying) are still viable under some circumstances. These cells can be killed by special storage processes at different temperatures. Dead cells may have intact or ruptured cell membranes, for example, but do not have any metabolic activity. Methods of producing killed cells may include, for example, a treatment with glass beads, where the effect of the shearing forces between the cells and the glass beads result in rupture of the cell. Other physical methods such as French press, high-pressure homogenization, ball mill or freeze-thaw processes and autoclaving result in killing of cells and also lead to fragments of the microorganisms according to the invention, as do UV irradiation, autolysis methods or special storage processes at different temperatures.

Whether a microorganism belonging to the genus of lactic acid bacteria has the properties according to the invention can be tested and verified by those skilled in the art, for example, on the basis of the tests described here and below. The term "*Lactobacillus* cells" may also be used in the sense of the present invention to include lactic acid bacteria or *lactobacilli* and includes microorganisms which require carbohydrates in particular glucose and lactose for fermentation of lactic acid and usually make use of the Embden-Meyerhof biosynthesis pathway. The *Lactobacillus* cells are taxonomically classified in the Lactobacteriaceae family. They are Gram-positive, non-spore-forming and in general are immobile. The *Lactobacillus* cells are anaerobic but are aerotolerant although they do not contain any hemins (cytochrome, catalase) (Schleifer et al., System. Appl. Microb. 18, 461-467 (1995) or Ludwig et al., System. Appl. Microb. 15, 487-501 (1992). The *Lactobacillus* cells and/or the species can be determined on the basis of the carbohydrate utilization pattern, in particular using the API test (from the company Biomerieux). According to the invention these include in particular species that are suitable for homofermentative lactic acid fermentation or heterofermentative lactic acid fermentation. Such *Lactobacillus* cells are preferably also selected from the group comprising *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentosus, Lactobacillus rhamnosus, Lactobacillus curvatus* and *Lactobacillus plantarum* (all of which are homofermentative), also *Lactobacillus brevis, Lactobacillus buchneri, Lactobacillus fructivorans, Lactobacillus hilgardii, Lactobacillus fermentum, Lactobacillus reuteri, Lactobacillus viridescens* as well as *Bifidobacterium bifidum, Lactobacillus ingluviei* (all of which are heterofermentative). *Lactobacillus* cells that are suitable as examples and have been deposited by the applicant include: *Lactobacillus paracasei* subspecies *paracasei* (DSM 25972), *Lactobacillus crispatus* (DSM 25987, DSM 25988), *Lactobacillus plantarum* (DSM 25989), *Lactobacillus ingluviei* (DSM 25973) all of which are preferred according to the present invention.

In a preferred embodiment of the present invention, the microorganism according to the invention is selected from *Lactobacillus paracasei* subspecies *paracasei, Lactobacillus crispatus, Lactobacillus plantarum, Lactobacillus ingluviei*, each of which has been deposited with the German Collection for Microorganisms and cell cultures (DSMZ) in Braunschweig under the deposition numbers DSM 25972, DSM 25987, DSM 25988, DSM 25989, DSM 25973. The above mentioned DSMZ depositions were done in accordance with the Budapest Treaty regarding International Recognition of the Deposition of Microorganisms for the purpose of patent deposition.

As mentioned above, the present invention also relates to compositions containing microorganisms, preferably viable, or analogs, mutants, derivatives or fragments thereof as well as preferably at least one vehicle or excipient selected from at least one of the following: a cosmetically acceptable vehicle or excipient, a pharmaceutically acceptable vehicle or excipient or a dermatologically acceptable vehicle or excipient.

The term "composition" in the sense of the present invention is understood to include in particular only a composition containing at least one microorganism according to the invention or a fragment, derivative, analog or mutant thereof as well as other optional ingredients such as vehicles or excipients or optionally other active ingredients and salts. Cosmetically, pharmaceutically or dermatologically acceptable additives, vehicles or excipients are understood to be any substances generally in cosmetic, pharmaceutical or dental fields to cosmetically or pharmaceutically use, administer or effectively apply an active ingredient or composition, i.e., in the present case at least one microorganism, analog or derivative or mutant or fragment thereof.

The term "mucosa" or "mucous membrane" in the sense of the present invention and the claims are understood to refer to the inner layer lining hollow organs kept moist by glandular secretions. In particular this refers to the oral and nasal mucosa, the connective tissue, the mucous membranes of the gastrointestinal tract and the mucous membranes of the chemical area.

"Inflammatory diseases" are understood within the context of the present description and patent claims to refer to diseases involving acute, subacute, chronically relaxing or chronically persistent disease states involving the skin, mucous membranes or the oral cavity. Inflammatory diseases are characterized clinically by redness, swelling, pain, itching, exudation, vasiculation, hyperkeratosis, hypersquamation, erosions, ulcers and other substance defects as well as scabs, vesicles and other efflorescences. Histologically inflammatory cells can be found in the corium and/or in the epidermis. "Inflammatory diseases" or "inflammatory states" in the sense of the present invention and the patent claims are understood to refer in particular to diseases and conditions such as, for example (but not exclusively) eczema, atopic eczema, seborrheic eczema, allergic or toxic contact eczema), psoriasis and other hyperkeratotic inflammations, acute and chronic wounds, pruriginous skin diseases as well as rare inflammations such as lichen ruber planus, granulomatous and parapsoriatic skin changes as well as the large group of autoimmune diseases with a skin manifestation. The term "prophylaxis" or "prevention" is understood in the present description and claims to include all types of prevention, namely both preventive treatment of healthy users and/or patients as well as preventive treatment of those users and/or patients who tend to have microbial diseases of the skin, mucous membranes or oral cavity or users and/or patients (persons with a so-called "predisposition") who tend to have inflammatory diseases. Furthermore, prevention is also understood to include preventive treatment of users and/or patients who have already suffered once from a microbial disease of the skin, mucous membranes or oral cavity or from an inflammatory disease and have overcome the disease in the meantime, for example, by successful treatment such as the treatment presented in the present description and claims (so-called "recurrence prevention"). Furthermore prevention in the sense of the present description and claims is also understood to include cosmetic treatment as well as the care and reparative treatment of skin which tends to develop irritation.

It is preferable that the composition may contain no only one of the microorganisms according to the invention or an analog, mutant, derivative or fragment thereof but also may contain a mixture of microorganisms according to the invention or a mixture of the analogs, derivatives, mutants or fragments or a mixture of the microorganisms according to the invention and fragments, derivatives, mutants or analogs thereof.

The composition may preferably be in an solid or liquid or viscous form or an aerosol and may be used, for example, in the form of powders, tablets, solutions, granules, suspensions, emulsions, capsules, pastes, gels, sprays, etc., i.e., in any form suitable for administration. It is also preferable if the composition comprises additional probiotics, antiseptics or other antibacterial substances and preferably but optionally saccharides and preservatives, flavorings, sweeteners, vitamins, minerals, aromas, etc. EP 2 133 414 A1 lists a number of ingredients that an be used for preferred compositions. Reference is made explicitly to this publication. Furthermore, fillers, flow control agents, rheology modifiers, softeners, stabilizers or reactively crosslinked monomers, for example, methacrylates may be present in a preferred composition. In this regard it may be preferable for the composition to contain substances such as EDTA, magnesium, calcium, SDS or the salts thereof or similar salts. It was completely surprising that these substances first inhibit the formation of a biofilm by *Streptococcus pyogenes* but also promote the coaggregation ability of the preferred microorganisms. The composition according to the invention is used in particular for administration in physical hygiene, treatment and prevention and contains at least one microorganism according to the invention or derivatives, mutants, fragments or analogs thereof.

It is preferable in particular to use the composition as a probiotic, i.e., as a preparation containing viable microorganisms that can be taken orally and has a health-promoting effect on the person taking the probiotic and/or the person to whom it is administered. Such preparations may be foods or food additives or animal feeds or feed additives or medications. According to the invention the composition may be used on all commercial animals and household pets, i.e., besides on humans also on dogs, cats, horses, camels, falcons, etc. The microorganisms and/or a composition containing them may be used in various ways to accomplish this. For example, it may be preferable to apply this composition in or to chewable bones, chew sticks, animal treats, animal feed, pellets, bitable and chewable articles or animal toys, etc. In particular it is preferable if the microorganisms or the composition is/are used for treatment and/or prevention of bacterial infections in the area of the throat, caused in particular by *Streptococcus pyogenes*, in animals and in humans.

The dosage and administration per se with which the composition according to the invention is used will depend on the specific use and the specific patient—in particular the age, weight, general condition, etc.—and are within the scope of abilities and assessment of those skilled in the art who will bring about the use of this composition.

The composition according to the invention may be a cosmetic product, a medical product or a pharmaceutical product. The composition preferably contains the lactic acid bacteria in an amount of 0.001 wt % to 20 wt %, preferably 0.005 wt % to 10 wt %, especially preferably 0.01 wt % to 5 wt %. It was completely surprising that the use of an amount of 0.001 wt % to 20 wt % in particular would result in decomposition being usable for a longer period of time, i.e., remaining stable. If the lactic acid bacteria are used in an amount of 0.005 wt % to 10 wt %, this surprisingly results in a positive effect on the rheological properties of the composition and results in the composition having a lower viscosity and thus being distributed better on the skin or being easier to introduce into the oral cavity. Use of the lactic acid bacteria in an amount of 0.01 wt % to 5 wt % has surprisingly resulted in the components of the composition bonding to one another better and the possibility of supplying a homogeneous composition in a reduced working time, which in turn leads to a reduction in the production costs. It is self-evident, however, that other amounts, which are different from those specified herein, may also be used for specific applications. It was especially surprising that the lactic acid bacteria according to the invention have an extremely high coaggregation activity in human saliva. The resulting aggregates with *Streptococcus pyogenes* have an extremely good stability and therefore can be removed very well and efficiently by rinsing or swallowing.

The coaggregation efficiency can surprisingly be increased significantly in the presence of cofactors (EDTA, $MgCl_2$, $CaCl_2$, SDS). It was absolutely unexpected that EDTA in particular would have a strongly positive effect on the coaggregation of lactic acid bacteria according to the invention with *Streptococcus pyogenes*. As mentioned also above, according to a preferred embodiment the composition and/or the microorganism may be used in the area of prevention and treatment of infections of the throat and tonsils to aggregate the aforementioned pathogenic microorganisms, i.e., to bind them. This coaggregation can be removed easily by swallowing or rinsing and/or in the case of a suspension they may be rinsed out in particular which advantageously achieves a reduction in the number of pathogens. The lactic acid bacteria and/or a composition containing same may be used for this purpose in a variety of ways. For example, they may be used in sprays, gargle solutions or mouth washes, as lozenges or throat tablets, pastilles, coated pills, aerosols, toothpaste, juices, syrup or as an additive in foods and/or as a food supplement. Therefore the present invention also relates to all products used in the area of physical hygiene and medical products and prophylaxis and containing the lactic acid bacteria according to the invention. The embodiments described above are considered accordingly for the areas of treatment, therapy and prevention in mammals. The microorganisms and/or compositions containing same may therefore be used in various ways.

It is preferably in particular if the composition according to the invention and/or the microorganisms according to the invention is/or used to produce a pharmaceutical drug, for treatment or prevention of throat symptoms, Pharyngitis atrophicans et sicca, Pharyngitis sicca, Angina lateralis, tonsillitis caused by *Streptococcus pyogenes*. The microorganisms and compositions according to the invention containing the same provide agents with which these diseases can be treated and/or prevented advantageously. The microorganisms and/or the compositions containing them may be used in both human and veterinary medicine, in particular in dogs, cats, horses, camels and falcons as already indicated. The composition and/or the microorganisms according to the invention—or fragments, derivatives or mutants thereof—may be used in particular as food additives, hygiene products and/or as a hygiene product containing the microorganisms or as a pharmaceutical preparation.

The present invention also relates to a method for identification and/or selection of a microorganism of the genus *Lactobacillus* sp. having the properties according to the invention, such that the method comprises at least the following steps: a) incubating a batch of a pathogenic microorganism selected from *Streptococcus pyogenes* for binding to fibronectin, b) adding the microorganism of the genus *Lactobacillus* to be investigated and incubating the batch to form the specific bond between the pathogenic microorganism and the microorganism of the genus to be investigated, c) separating the unbound microorganisms of the *Lactobacillus* genus by removing the supernatant and d) determining the fibronectin binding with regard to bound and aggregated microorganisms of the *Lactobacillus* genus.

In a preferred embodiment the method according to the invention also comprises the step of investigating the prevention of fibronectin binding by *Streptococcus pyogenes*. The microorganisms of the *Lactobacillus* genus to be investigated were added here during the incubation of the fibronectin-binding fluorescence-labeled pathogenic microorganism. After removing the unbound cells, specific quantification of the binding to fibronectin is preferably performed by measuring the fluorescence in comparison with controls by adding the microorganisms to be tested.

It is self-evident that the features mentioned above and those yet to be described below may be used not only in the particular combination given but also alone without going beyond the scope of the present invention.

DESCRIPTION OF THE FIGURES

Additional advantages are derived from the following figures and the experiments conducted in this regard as well as the exemplary embodiments. The experiments were performed using all the preferred lactic acid bacteria although only a few of the experiments are presented here. Those skilled in the art can reproduce the invention on the basis of the examples, in which.

DETAILED DESCRIPTION OF THE EXEMPLARY EMBODIMENTS

Example 1

For identification and selection of microorganisms according to the invention, various strains from a *Lactobacillus* strain bank were tested by a four-step screening process in which they were first screened with regard to the ability to bind to the target pathogenic microorganism *Streptococcus pyogenes* (hereinafter also referred to as the "target microorganism") (binding assay) and then the strains identified in the first step were tested in a coaggregation assay in the microtiter plate scale, where the coaggregation with the respective target microorganism was measured qualitatively using a binocular stereo microscope. In the sense of the present invention, the term "co-aggregation" is used as synonymous with the term "coaggregation." Furthermore, the intensity of coaggregation and the stability of the binding to the target microorganism as well as the ability to prevent binding to fibronectin were investigated, ultimately leading to the exemplary microorganisms according to the invention that were identified (*Lactobacillus*).

Binding Assay

A binding assay was established to permit quantification of the binding activity of selected *Lactobacillus* strains, permitting quantitative detection of the binding of *Lactobacillus* strains to pathogenic microorganisms in a 96-well plate. The binding activity of the *Lactobacillus* cells with the target microorganism correlates with the coaggregation activity and/or coaggregation capability. This was tested experimentally.

Figure 2:
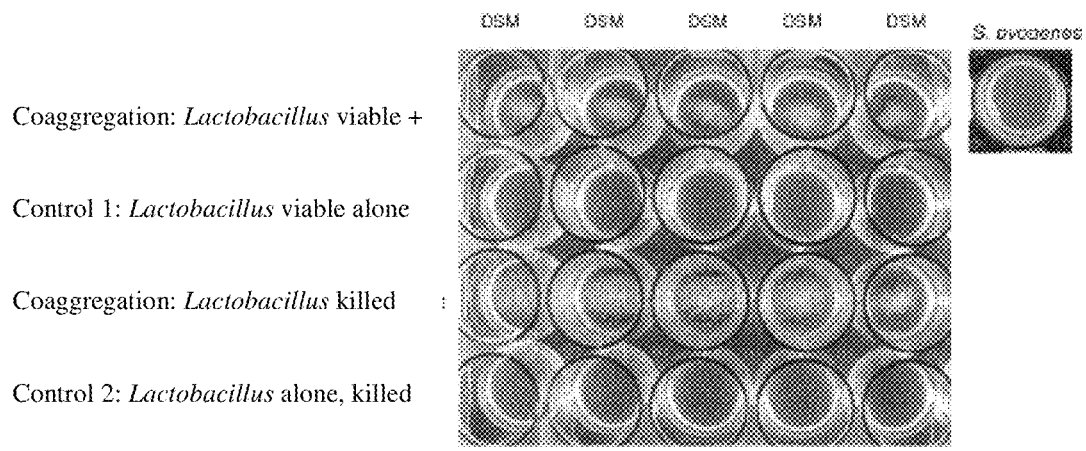
FIG. 2 shows the macroscopic controls (photograph of a 24-well microtiter plate) of the specific binding of an exemplary embodiment of a microorganism according to the invention (DSM 25972, DSM 25987, DSM 25988, DSM 25989 and DSM 25973) to *Streptococcus pyogenes* in the coaggregation batch in the 24-well scale as well as the *Lactobacillus* strains according to the invention and the *Streptococcus pyogenes* target strain, both alone and in a photo documentation system. A white precipitant is formed by coaggregation (and the associated precipitation). The agglomerate then results in *Streptococcus pyogenes* in particular being unable to bind to the epithelial cells of the throat. Tests on patients have shown that bacterial infections can be prevented or reduced by means of the preferred microorganisms.

In this regard, FIG. 2 shows an example of coaggregation of the *Lactobacillus* DSM 25972, DSM 25987, DSM 25988, DSM 25989 and DSM 25973 and *Streptococcus pyogenes* ATCC 19615.

The measurement method is based on the specific binding of the strains according to the invention to a target strain bound in a biofilm. Defined amounts of the strains according to the invention were labeled with a fluorescent dye (CFDA solution, Invitrogen) and were mixed with a defined amount of target microorganisms bound to a biofilm for the assay. The persistence of the bound strains according to the invention on the target strain is measured using a fluorescence photometer after washing several times.

To perform these tests the target microorganisms *Streptococcus pyogenes* was cultured according to the standard protocol. The strain was cultured in THY (Todd Hewitt broth) medium under aerobic conditions at 37° C. in a 5% $CO_2$ atmosphere. The *Lactobacillus* strains were cultured anaerobically ad 37° C. in MRS medium (see de Man et al. (1960) "A medium for the cultivation of *Lactobacilli*," J. Appl. Bact. 23 (130-135). For workup of the target microorganism, the cells were harvested after 5 to 6 hours of culturing in the average exponential growth phase, then washed three times with PBS (phosphate-buffered saline, pH 7.4) and dissolved in PBS. To do so 100 μL of the suspension was placed in each well of a 96-well microtiter plate. During a 16-hour incubation at 37° C. in 5% $CO_2$, a biofilm is formed by the target microorganism. After incubation, unbound cells were removed by washing three times with phosphate-buffered saline (PBS, pH 7.4). For processing of the *Lactobacillus* strains, they were harvested after culturing for 24 hours then washed three times with PBS, placed in PBS and labeled with fluorescence by adding the CFDA solution (Invitrogen). To perform the binding assay, 100 μL of the fluorescence-labeled *Lactobacillus* suspension was added per well to the target strain bound in a biofilm. Control batches without addition of the *Lactobacillus* suspension were carried in parallel. After incubating for 1 hour at 37° C. in an incubator, the unbound cells were separated and washed three times with PBS. After each washing step the fluorescence was measured in a fluorescence plate photometer (Em 485 nm/Ex 535 nm). The increase in fluorescence (Em 485 nm/Ex 535 nm) in the batch with the *Lactobacillus* strains in comparison with the controls without *Lactobacillus* cells correlated with the amount of biofilm-bound *Lactobacillus* cells. The measured fluorescence after binding of the *Lactobacillus* cells corresponded to the binding intensity. The higher this value, the better the binding of the labeled *Lactobacillus* cells to the target strains bound in the biofilm and the greater the binding activity of the *Lactobacillus* cells tested.

Figure 1:
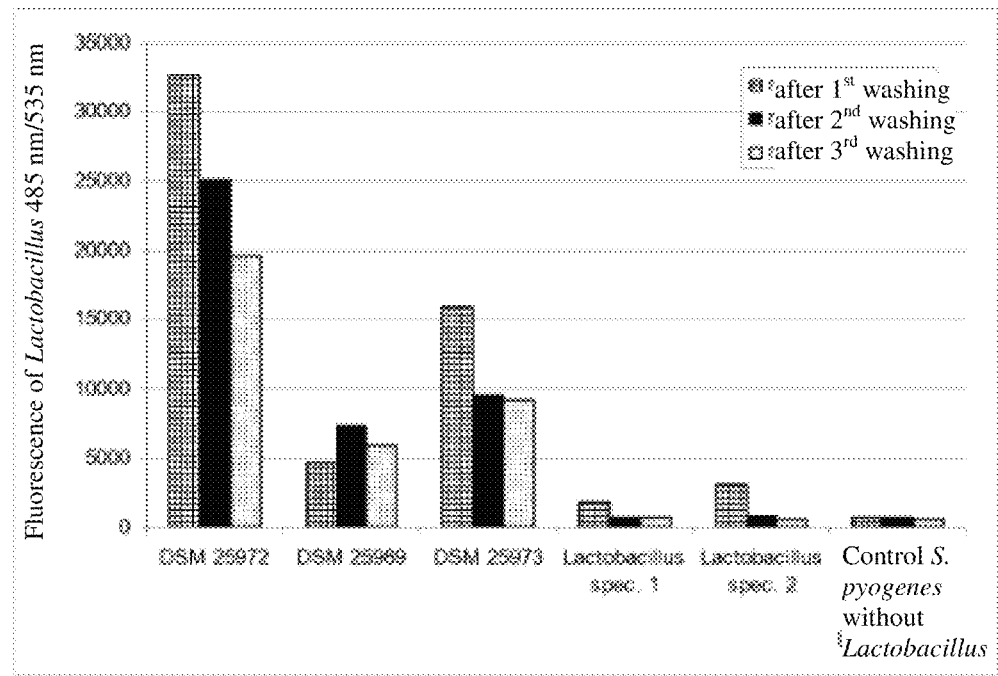
FIG. 1 shows the specific binding and/or aggregation of one exemplary embodiment of the microorganisms according to the invention (DSM 25972, DSM 25989, DSM 25973) to a biofilm formed by *Streptococcus pyogenes* (binding assay) after washing the unbound cells three times and, for comparison with that, additional *Lactobacillus* strains that are not according to the invention and are not capable of binding to *Streptococcus pyogenes* (*Lactobacillus* species 1 and *Lactobacillus* species 2); specific quantification of the binding and/or aggregation of CFDA-labeled *Lactobacillus* strains according to the invention to the *S. pyogenes* biofilm in 96-well microtiter plates based on fluorescence measurement (Ex485 nm/Em535 nm). In this way, those skilled in the art will learn that the preferred microorganisms can be used in bacterial infections that occur especially in the oropharyngeal area in particular.

These experiments have shown that for the target microorganism *Streptococcus pyogenes* in the binding assay after removal of the unbound cells, the *Lactobacillus* strains according to the invention lead to an increase in the fluorescence by a factor of up to 17 due to the binding of the labeled *Lactobacillus* cells to the target strains bound in the biofilm after three washings. FIG. 1 shows the results of the binding assay for *Lactobacillus* DSM 25972, DSM 25989 and DSM 25973 with *Streptococcus pyogenes* as exemplary for the microorganisms according to the invention. For comparison purposes, FIG. 1 also shows the data on *Lactobacillus* strains not according to the present invention (*Lactobacillus* species 1 and 2) which are not capable of specific binding for the target microorganism. It is found that the preferred microorganisms are capable of preventing bacterial infections in humans and animals and/or are used for treatment of same because they coaggregate specifically with *Streptococcus pyogenes*. In this way binding of *Streptococcus pyogenes* to epithelial cells is prevented on the one hand while on the other hand the formation of biofilm by *Streptococcus pyogenes* is prevented or any biofilm already formed is dissolved or broken up.

Example 2

Coaggregation Assay

The following verification in a 1.0 mL volume and/or in a 24-well plate is used to illustrate the coaggregation activity of selected *Lactobacillus* strains.

In this method, the coaggregation behavior of the *lactobacilli* and of the target strain is considered separately and finally the coaggregation of *Lactobacillus* and the target strain together in a mixture is considered. This analysis is performed macroscopically by using photographs of the 24-well plate as well as microscopically. To perform these tests, the target microorganism, *Streptococcus pyogenes*, was cultured according to standard protocols. The strain was cultured in THY (Todd Hewitt broth) medium under aerobic conditions, in 5% $CO_2$ atmosphere at 37° C. The *Lactobacillus* strains were cultured in MRS medium (see de Man et al. (1960) "A medium for the cultivation of *lactobacilli*," J. Appl. Bact. 23 (130-135)) anaerobically at 37° C. For workup of the target microorganism, the cells were harvested in the middle exponential growth phase after 5 to 6 hours of culturing, washed twice with phosphate-buffered saline (PBS, pH 7.4) and adjusted to $OD_{600}$=4. For workup of the *Lactobacillus* strains, they were harvested after culturing for 16 hours, washed twice with PBS then placed in a volume of PBS and adjusted to an $OD_{600}$=4 accordingly. To perform the coaggregation assay, 500 μL portions of a target microorganism suspension per well were combined with 500 μL *Lactobacillus* suspension in a 24-well plate. Control batches with 500 μL of the target microorganism plus 500 μL PBS or 500 μL of the respective *Lactobacillus* suspension plus 500 μL PBS (control 1) were tested in parallel. After incubating for 10 minutes at 25° C. on a desktop agitator, the batches were observed macroscopically by using a photo documentation system in addition to being observed microscopically. For analysis of the coaggregation capability of the killed *Lactobacillus* cells, they were first killed by a heat treatment at 70° C. for 30 minutes in a water bath and then used in the coaggregation assay.

Figure 3:
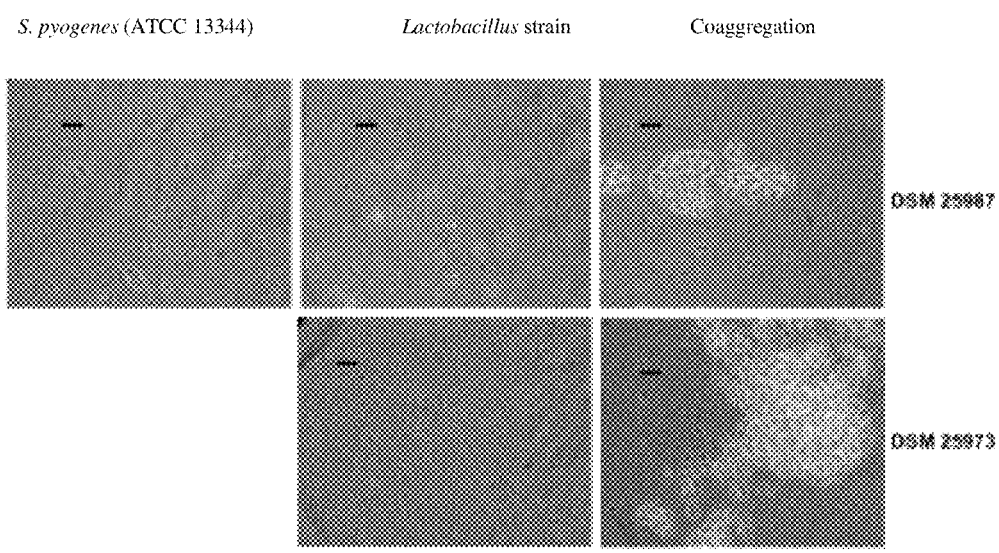
FIG. 3 shows the microscopic representation of the specific binding of an exemplary embodiment of a microorganism according to the invention (DSM 25987 and DMS 25973) to *Streptococcus pyogenes* cells after coaggregation as well as the *Lactobacillus* strains according to the invention and the *Streptococcus pyogenes* alone. Microscopic imaging (phase contrast, 1000× magnification); coaggregates can be seen as large cell agglomerates.

These experiments showed that the selected *Lactobacillus* strain would coaggregate with the target microorganism *Streptococcus pyogenes*, so that it is possible to observe clumping (aggregates) in the mixture, which are visible macroscopically by irregular condensed and/or granular regions in the well. There is no clumping or formation of aggregate in the wells containing the target strain and/or the *Lactobacillus* strains according to the invention separately. The cell suspension in the well remains homogeneous. FIG. 2 shows the macroscopic results in the coaggregation batch for the selected *Lactobacillus* strains, both alive and killed for the target microorganism *Streptococcus pyogenes*. In the microscopic observation, there is a clear-cut affinity for the target microorganism in all the *Lactobacillus* strains according to the invention, leading to different aggregate sizes in microscopic observation of coaggregation. FIG. 3 shows the microscopic results in the coaggregation batch for the *Lactobacillus* strains DSM 25987 and DSM 25973 according to the invention for the target microorganism *Streptococcus pyogenes*, for example. The preferred microorganisms are capable of preventing or combatting bacterial infections caused by *Streptococcus pyogenes* and/or in which *Streptococcus pyogenes* is involved, in particular in patients or animals.

Example 3

Coaggregation in Human Saliva

To investigate the coaggregation capability of the *Lactobacillus* strains according to the invention in natural human saliva, they were harvested after 16 hours of culturing as described in Example 2, washed twice in PBS and placed in human saliva. The saliva had previously been collected from several people, mixed and separated from the particles by centrifugation at 8000 g at 20 minutes. The target microorganism was worked up as described in Example 2 and was likewise placed in human saliva after washing twice in PBS. To perform the coaggregation assay, 500 µL portions of the target microorganism suspension in saliva were combined with 500 µL *Lactobacillus* suspension in saliva per well in a 24-well plate. Control batches with 500 µL of the target microorganism plus 500 µL saliva or 500 µL of the respective *Lactobacillus* suspension plus 500 µL saliva (control 1) were carried in parallel. After incubating for 10 minutes at 25° C. on a desktop agitator, the batches were observed macroscopically by means of a photo documentation system as well as being observed microscopically.

Figure 4:
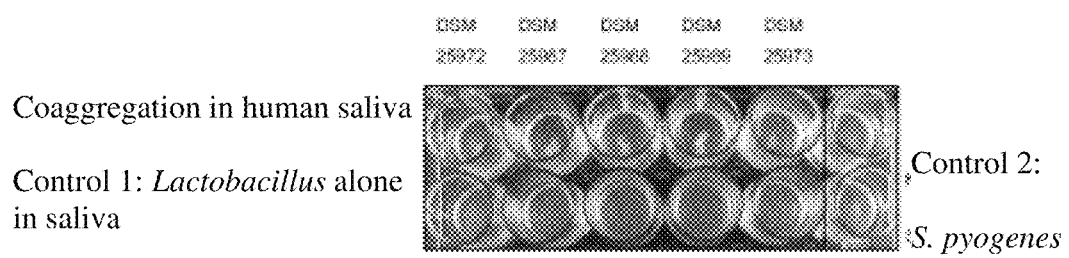
FIG. 4 shows the macroscopic control (photograph of a 24-well microtiter plate) of the specific binding of an exemplary embodiment of a microorganism according to the invention (DSM 25972, DSM 25987, DSM 25988, DMS25989 and DMS25973) to *Streptococcus pyogenes* cells (coaggregation) in human saliva as well as the *Lactobacillus* strains according to the invention and *Streptococcus pyogenes* alone in a photo documentation system. A white deposit is also caused by coaggregation (and the associated precipitation). It was surprising that the preferred microorganisms already bind to *Streptococcus pyogenes* in saliva, in particular coaggregating there and thus preventing binding of *Streptococcus pyogenes* to epithelial cells. It was also surprising that the preferred microorganisms did not lose their preferred capabilities due to the enzymes present in saliva. Therefore the preferred microorganisms are advantageous for use in an oral application agent such as a bonbon in particular.

Tests have shown that the *Lactobacillus* strains according to the invention in natural saliva are capable of a specific coaggregation with the target microorganism *Streptococcus pyogenes*. This provides the best prerequisites for application of the *Lactobacillus* strains according to the invention in the oropharyngeal space. The preferred microorganisms for this may be administered orally as a bonbon, for example, and lead to relief or even complete treatment of bacterial infections. FIG. 4 shows the macroscopic results of coaggregation in natural human saliva for the *Lactobacillus* strains according to the invention with the target microorganism *Streptococcus pyogenes*.

Example 4

Preventing Binding to Fibronectin

Figure 5:
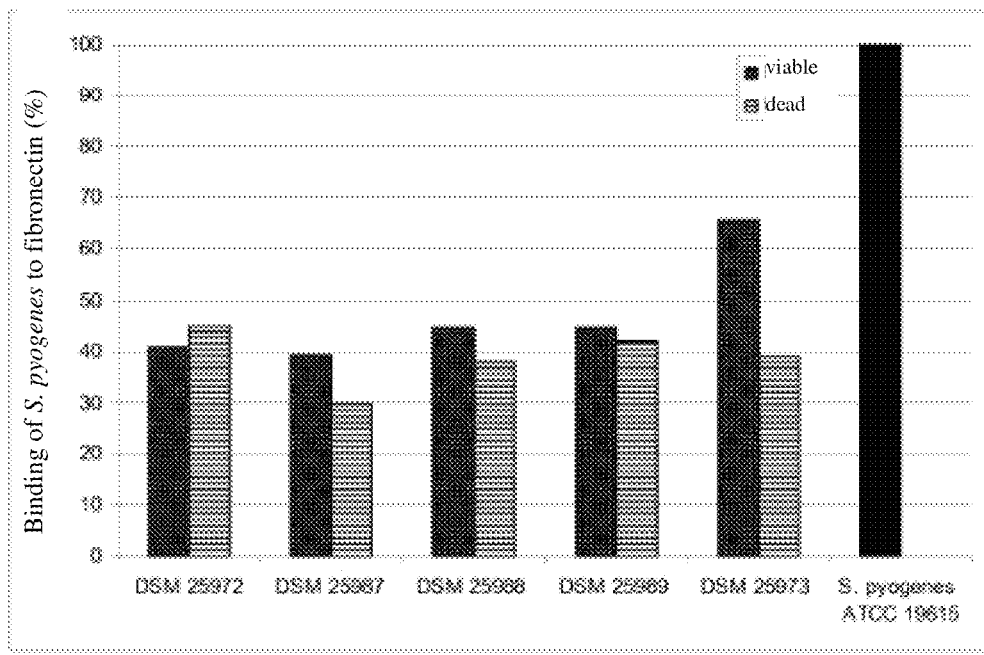
FIG. 5 shows the influence of an exemplary embodiment of the microorganisms according to the invention (DSM 25972, DSM 25987, DSM 25988, DSM 25989 and DSM 25973) on the prevention of fibronectin binding of *Streptococcus pyogenes* strain ATCC 19615 after 2 hours of incubation at 37° C. with *Lactobacillus* suspension (viable) washed in PBS and *Lactobacillus* suspension (dead) killed by a heat treatment. Specific quantification is the binding of CFDA-labeled *Streptococcus pyogenes* to the 96-well microtiter plate coated with fibronectin. This shows the binding of *Streptococcus pyogenes* in percent, where 100% represents the binding of *S. pyogenes* (ATCC 19615) alone to the fibronectin coating of the microtiter plate without the addition of *Lactobacillus* suspension. It is found that the preferred microorganisms prevent binding of *Streptococcus pyogenes* to epithelial cells in the throat and thus also prevent bacterial infection.

To investigate the effect of the *Lactobacillus* strains according to the invention on the binding of the target pathogenic microorganism *Streptococcus pyogenes* (ATCC 19615) to fibronectin, a binding assay which permits quantitative detection of the binding of fluorescence-labeled target microorganism in a fibronectin-coated 96-well plate was established. The *Lactobacillus* strains according to the invention were added directly to the CFDA-labeled target microorganism at the start of the binding and incubated for 2 hours at 37° C. After removing the unbound cells and washing twice with PBS, the specific quantification of the bound target microorganism cells was performed by measuring the fluorescence at Em 485 nm/Ex 535 nm in the fluorescence plate photometer. To perform these tests, target strains and the *Lactobacillus* strains according to the invention were cultured according to standard protocols. For workup of the *Lactobacillus* strains they were washed twice in PBS after culturing and then were placed in PBS. Some of the *Lactobacillus* strains were killed by pasteurization at 70° C. for 30 minutes after washing in PBS. For workup of the target strain, it was cultured for 16 hours until reaching the steady state growth phase, then harvested, labeled by adding CFDA fluorescence and adjusted to $OD_{600nm}=3.0$. To perform the binding assay the *Lactobacillus* cells were added directly to the fluorescence-labeled target microorganism at the start of the binding and were incubated for 2 hours under microaerophilic conditions at 37° C. Control batches without addition of the *Lactobacillus* suspension were carried in parallel. After removing the planktonic cells and washing the cells found in the biofilm, the specific quantification of the bound target microorganism cells was performed by fluorescence measurement with and without *Lactobacillus* cells. The reduction in fluorescence in comparison with the controls of the target microorganism without *Lactobacillus* correlated with the intensity of the binding of the target microorganism *Streptococcus pyogenes* to the fibronectin-coated microtiter plate. This reduction is represented at the percentage hindrance of biofilm formation. FIG. 5 shows the results obtained with *Lactobacillus* strains DSM 25972, DSM 25987, DSM 25988, DSM 25989 and DSM 25973 in hindering the binding to fibronectin; these strains were tested as an example of the microorganisms according to the present invention, namely *Streptococcus pyogenes* ATCC 19615. Experiments have shown that this leads to hindered binding of target microorganisms to fibronectin due to the *Lactobacillus* strains according to the invention as listed above in both viable and killed form. Therefore, this shows that the *Lactobacillus* strains according to the invention are capable of preventing binding of *Streptococcus pyogenes* to host cells. Furthermore, experiments with additional microorganisms of the same genus and species were also performed in order to depict the specificity of the binding properties and/or the aggregation properties of the *Lactobacillus* strains according to the invention as well as their ability to prevent binding to fibronectin as a function of the target microorganisms of the same genus and species. *Streptococcus pyogenes* ATCC 12344, among others, was selected for this purpose. To investigate their effect on the binding of the target microorganism *Streptococcus pyogenes* ATCC 12344 to fibronectin, the *Lactobacillus* strains according to the invention and the target microorganism were cultured under standard conditions as described above, then worked up and used in the assay.

Figure 6:
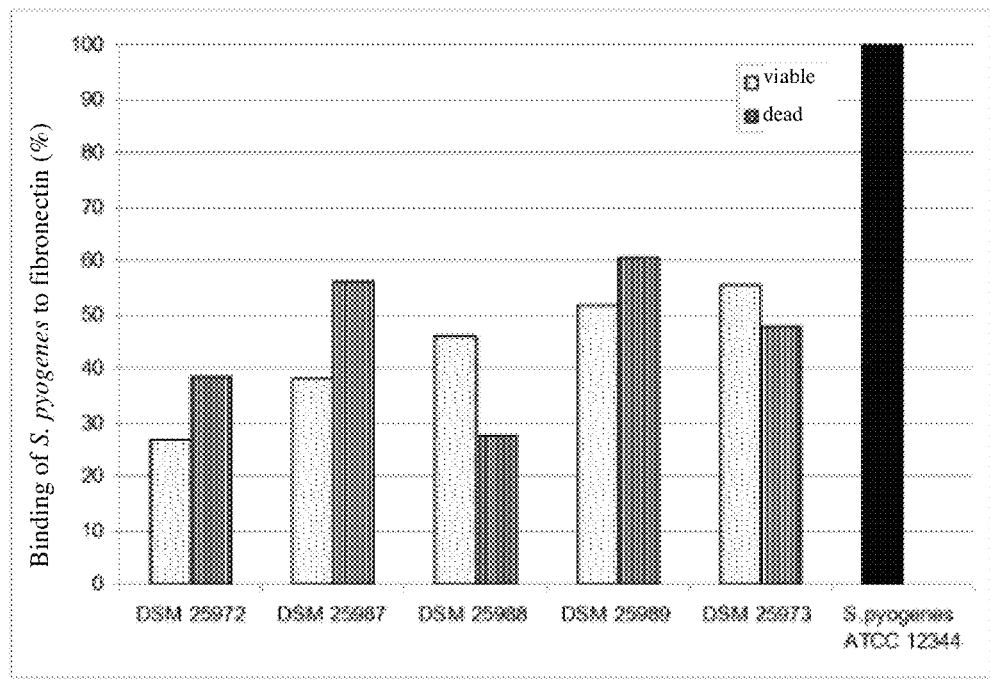
FIG. 6 shows the influence of one exemplary embodiment of the microorganisms according to the invention (DSM 25972, DSM 25987, DSM 25988, DSM 25989 and DSM 25973) on the binding of *Streptococcus pyogenes* (strain ATCC 12344) to fibronectin after 2 hours of incubation at 37° C. (with *Lactobacillus* suspension (viable) washed in PBS and *Lactobacillus* suspension (dead), wherein the *Lactobacillus* is killed by heat treatment). This shows specific quantification of the binding of CFDA-labeled *Streptococcus pyogenes* to the fibronectin-coated 96-well microtiter plate. This shows the binding of *Streptococcus pyogenes* in percent, where 100% represents binding of *S. pyogenes* alone to the fibronectin coating of the microtiter plate without the addition of *Lactobacillus* suspension.

Tests have shown that other microorganisms of the same species and genus can also be aggregated by the *Lactobacillus* strains according to the invention and that the *Lactobacillus* strains according to the invention can also prevent other target microorganisms from binding to fibronectin. FIG. 6 shows the results in preventing binding of *Streptococcus pyogenes* (strain ATCC 12344) to fibronectin by the *Lactobacillus* strains DSM 25972, DSM 25987, DSM 25988, DSM 25989 and DSM 25973 as exemplary of the microorganisms according to the invention. It was completely surprising that administering preferred microorganisms to humans or animals could be utilized to prevent or treat bacterial infections, whereby additional microorganisms of the same genus and species as *Streptococcus pyogenes* may also be involved in the infection.

Example 5

Coaggregation of *Streptococcus salivarius*

Figure 7:
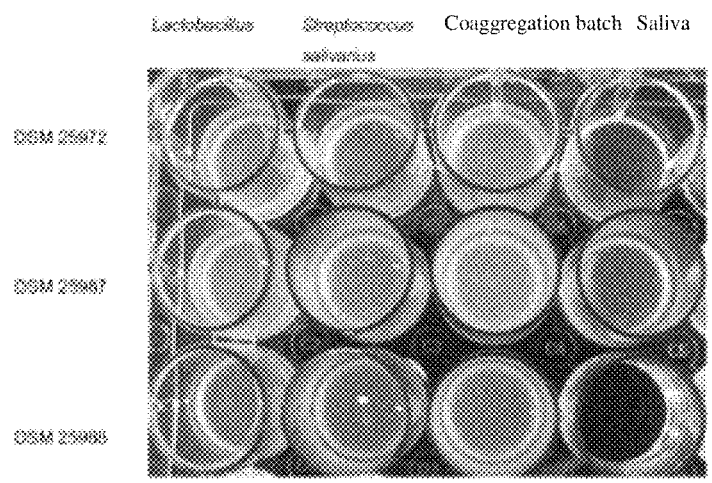
FIG. 7 shows the macroscopic representation (photograph of a 24-well microtiter plate) of coaggregation of one exemplary embodiment of the microorganism according to the invention (DSM 25972, DSM 25987, DSM 25988, DMS 25989 and DMS 25973) and *Streptococcus salivarius* in PBS buffer as well as the *Lactobacillus* strains according to the invention and *Streptococcus salivarius* alone in a photographic documentation system. The white deposit is formed by coaggregation (and the resulting precipitation).

*Lactobacillus* strains according to the invention and *Streptococcus salivarius* were cultured according to standard conditions, washed three times in PBS and used in human saliva in the coaggregation assay. The results show that *Streptococcus salivarius* is not coaggregated by the *Lactobacillus* strains according to the invention (FIG. 7). The possibility can thus be ruled out that commensal strains, represented here by *Streptococcus salivarius* as an example, are not coaggregated by *Lactobacillus* strains and removed from their natural habitat. This shows in particular that the preferred lactic acid bacteria have a specific action against bacterial infections.

REFERENCE LIST

[S.=page; und=and; Hrsg.=ed./eds.; Kapitel=chapter]

Beachey und Ofek (1976) Epithelial cell binding of Group A Streptococci by lipoteichoic acid on fimbriae denuded of M protein. Journal of experimental medicine 143:759-771

Bisno (1995) *Streptococcus pyogenes* S. 1786ff in Marndell. Bennett und Dolin (Hrsg.) Principles and practice of infectious diseases. Vol 2. Churchill Livingstone, N.Y.

Courtney et al. (1999) Strategies for prevention of group A streptococcal adhesion and infection. S 553ff. In An und Friedman (Hrsg.) Handbook of bacterial adhesion: principles, methods, and applications. Humana Press, Totowa, N.J.

Cunningham (2000) Pathogenesis or group A streptococcal infections. Clin Microbiol Rev 13:470-551

Hasty et al. (1992) Multiple adhesins of streptococci. Infect Immun 60:2147-2152

Kaplan (1991) The resurgence of group A streptococcal infections and their sequelae. Eur J Clin Microbiol Infect Dis 10:55-57

Kilian (2002) *Streptococcus* and *Enterococcus*. In: Medical Microbiology, Greenwood, D.; Slack R C A.; Peutherer, J. F. (Hrsg.) Kapitel 16. Churchill Livingstone, Edingburgh, UK: pp 174-188, 2002

LaPenta et al. (1994). Group A streptococci efficiently invade human respiratory epithelial cells. Proc. Natl. Acad. Sci. USA 91:12115-12119

Musser und Krause (1998) The revival of group A streptococcal diseases, with a commentary on staphylococcal toxic shock syndrome. In Emerging Infections. Krause (Hrsg.) Academic Press, New York Reid et al. (2001) Group A *Streptococcus*: Allelic variation, population genetics, and host pathogen interactions. J Clinic Invest 107:393-399

Simpson und Beachey (1983) Adherence of group A streptococci to fibronectin on oral epithelial cells. Infect Immun 39:275-279

The invention claimed is:

1. A method for identifying and/or selecting a lactic acid bacterium that coaggregates with *Streptococcus pyogenes*, wherein the method comprises:

incubating *Streptococcus pyogenes* under conditions under which *Streptococcus pyogenes* forms a biofilm, adding the lactic acid bacterium to be investigated to a mixture for coaggregation between the *Streptococcus pyogenes* and the lactic acid bacterium and incubation of the mixture, and separating any unbound lactic acid bacteria by removing a supernatant and determining a presence of coaggregated lactic acid bacteria in the biofilm formed by *Streptococcus pyogenes*.

2. The method according to claim 1, wherein the lactic acid bacterium to be investigated is added during the incubation of the *Streptococcus pyogenes* which forms the biofilm.

3. The method according to claim 1 additionally comprising:

quantifying biofilm formation after removing the unbound lactic acid bacteria via measurement of an optical density in comparison with a control without addition of the lactic acid bacteria to be investigated.

4. A method for coaggregation comprising: administering to a patient in need of treatment, prophylaxis and/or therapy of microbial diseases or inflammatory diseases of the skin, mucous membranes or oral cavity a microorganism belonging to the lactic acid bacterium order, wherein the microorganism is *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gassed, Lactobacillus johnsonii, Lactobacillus paracasei, Lactobacillus pentosus, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus fermentum, Lactobacillus reuteri, Lactobacillus viridescens, Bifidobacterium bifidum* or *Lactobacillus ingluviei*, wherein the lactic acid bacterium administered aggregates at least with *Streptococcus pyogenes*.

5. The method of claim 4, wherein the patient is in need of topical treatment or prophylaxis.

6. The method of claim 4, wherein the microorganism of the lactic acid bacterium order coaggregates with the *Streptococcus pyogenes* even after a biological, chemical or physical treatment.

7. The method of claim 4, wherein the microorganism of the lactic acid bacterium order coaggregates with the *Streptococcus pyogenes* at a pH between approximately 3 and approximately 8.

8. The method of claim 4, wherein the microorganism of the lactic acid bacterium order inhibits the formation of a biofilm of the *Streptococcus pyogenes*.

9. The method of claim 4, wherein the microorganism of the lactic acid bacterium order prevents binding of fibronectin by *Streptococcus pyogenes*.

10. The method of claim 4, wherein the microorganism of the lactic acid bacterium order does not coaggregate with any commensal microorganism of the skin or mucous membranes.

11. The method of claim 4, wherein the microorganism of the lactic acid bacterium order is selected from the group consisting of the following microorganisms that have been deposited with the German Collection for Microorganisms and Cell Cultures and have been numbered as DSM 25972, DSM 25987, DSM 25988, DSM 25989 and DSM 25973.

12. The method of claim 4, wherein the microorganism is contained in an antimicrobial additive and inflammation in an oropharyngeal space and infection of the upper respiratory tract and skin are treated.

13. The method of claim 4, wherein the administration is orally, sublingually or buccally.

14. The method of claim 4, wherein said microorganism of the lactic acid bacterium order is administered as part of a composition comprising a pharmaceutically or cosmetically acceptable vehicle or excipient.

15. The method of claim 14, wherein the composition is in a solid, liquid or viscous form or is an aerosol, or wherein the composition is in the form of a paste, a soft gelatin capsule, hard gelatin capsule, powder, granules, beads, pastilles, effervescent tablet, lozenge, buccal tablet, chewable tablet, sublingual tablet, solution, tincture, emulsion, juice, concentrate, syrup, spray, drinking ampoule, gel, mouth wash, toothpaste, chewing gum, tablet, coated pill or bonbon.

16. The method of claim 14, wherein the composition comprises probiotics, antiseptics or other antibacterial substances.

17. The method of claim 14, wherein the composition is a pharmaceutical, veterinary or cosmetic composition or a food supplement or a food supplement composition.

18. The method of claim 14 additionally comprising one or more of the following substances: antioxidants, vitamins, coenzymes, fatty acids, amino acids and/or cofactors and/or one or more thickeners, one or more sweeteners and/or one or more artificial sweeteners.

19. The method of claim 18, wherein the thickener is selected from the group consisting of cellulose ether, polysaccharides, selected from the group comprising xanthan gum, gelatin, highly-disperse silicon dioxide, starch, alginates, tragacanth, agar, gum arabic, pectin and polyvinyl ester and the sweetener is selected from the group consisting of glucose, fructose, sucrose and glucose syrup, sorbitol, mannitol, xylitol and maltitol, saccharine, sodium cyclamate, acesulfame K, aspartame and combinations thereof.

20. The method of claim 14, wherein the microorganism is present as a viable or killed microorganism in the composition and/or is in encapsulated, spray-dried and/or lyophilized form and/or in form of a cell lysate.

21. The method of claim 14, wherein the microorganism is present in an amount of 0.001 wt % to 20 wt %.

22. The method of claim 21, wherein the microorganism is present in an amount of 0.005 wt % to 10 wt %.

23. The method of claim 21, wherein the microorganism is present in an amount 0.01 wt % to 5 wt %.

24. The method of claim 14, wherein the composition administered additionally comprises one or more flavoring substances.

25. The method of claim 24, wherein the composition is in form of a chewable compound, a chewing gum, a bonbon, a pastille, a toothpaste, a spray or a mouth wash.

26. The method of claim 14, wherein one or more anti-inflammatory and/or antimicrobial substances are additionally used in the composition administered and/or the composition administered is used in combination with solvents, vehicles, excipients, fillers, flavoring substances and/or aroma substances and/or additional ingredients.

27. The method of claim 14, wherein the composition is used prophylactically or curatively.

28. The method of claim 14 additionally comprising builder substances, enzymes, electrolytes, pH regulators, thickeners, soil release agents, optical brighteners, graying inhibitors, dye transfer inhibitors, film regulators and/or coloring agents.

* * * * *